(12) United States Patent
Sasai et al.

(10) Patent No.: US 8,224,820 B2
(45) Date of Patent: Jul. 17, 2012

(54) INFORMATION PROCESSING SYSTEM

(75) Inventors: Kosuke Sasai, Kobe (JP); Yasushi Matsumura, Ikeda (JP); Keunsik Park, Suita (JP); Toshiaki Nakano, Moriguchi (JP); Naoaki Suganuma, Kakogawa (JP)

(73) Assignees: Konica Minolta Medical & Graphic, Inc., Tokyo (JP); National University Corporation Oskaka University, Osaka (JP); Keunsik Park, Osaka (JP); Toshiaki Nakano, Osaka (JP); Naoaki Suganuma, Hyogo (JP)

( * ) Notice: Subject to any disclaimer, the term of this patent is extended or adjusted under 35 U.S.C. 154(b) by 174 days.

(21) Appl. No.: 11/600,412

(22) Filed: Nov. 16, 2006

(65) Prior Publication Data

US 2007/0143150 A1    Jun. 21, 2007

(30) Foreign Application Priority Data

Nov. 17, 2005   (JP) ................................ 2005-333181

(51) Int. Cl.
*G06F 7/00* (2006.01)
*G06F 17/30* (2006.01)

(52) U.S. Cl. ........ 707/736; 707/758; 707/802; 707/828; 707/941; 707/956; 715/200

(58) Field of Classification Search .................. 709/224, 709/203, 229, 223; 726/22; 707/1, 4, 101, 707/200, 791, 802, 828, 941, 956, 736, 758; 715/234, 200
See application file for complete search history.

(56) References Cited

U.S. PATENT DOCUMENTS

| 5,604,898 | A | * | 2/1997 | Saijyo et al. ...................... 707/4 |
| 5,696,980 | A | * | 12/1997 | Brew ............................ 704/273 |
| 5,926,463 | A | * | 7/1999 | Ahearn et al. ................ 370/254 |
| 6,208,993 | B1 | * | 3/2001 | Shadmon ............................. 1/1 |
| 6,425,007 | B1 | * | 7/2002 | Messinger .................... 709/224 |
| 6,910,103 | B2 | * | 6/2005 | Danan ........................... 711/118 |
| 7,051,012 | B2 | * | 5/2006 | Cole et al. ......................... 705/3 |
| 7,305,614 | B2 | * | 12/2007 | Chen et al. .................... 715/230 |
| 2002/0007411 | A1 | * | 1/2002 | Shaked et al. ............... 709/229 |
| 2002/0049810 | A1 | * | 4/2002 | Fitzgerald et al. ........... 709/203 |
| 2002/0078819 | A1 | * | 6/2002 | Kim ............................... 84/609 |
| 2003/0084349 | A1 | * | 5/2003 | Friedrichs et al. ............ 713/201 |

(Continued)

FOREIGN PATENT DOCUMENTS

JP          09-231230          9/1997

(Continued)

OTHER PUBLICATIONS

Office Action in Japanese Application No. JP 2005-333181, dated Jul. 23, 2009, 8 pages including English language translation.

*Primary Examiner* — Giovanna Colan
(74) *Attorney, Agent, or Firm* — Brinks, Hofer, Gilson & Lione

(57) ABSTRACT

The present invention provides a technique for supporting accurate and smooth creation of a report. Information in which elements belonging to items included in a plurality of items of elements constructing a report are associated with each other between the items is stored in an input support database. Partial information corresponding to an extraction condition designated by an input from an input client by the user is extracted from the input support database and visually output (displayed) in a view in a report creating area.

52 Claims, 18 Drawing Sheets

U.S. PATENT DOCUMENTS

| | | | |
|---|---|---|---|
| 2003/0130997 A1* | 7/2003 | Enewoldsen et al. | 707/3 |
| 2004/0107204 A1* | 6/2004 | Sakamoto | 707/101 |
| 2004/0168119 A1* | 8/2004 | Liu et al. | 715/501.1 |
| 2004/0267825 A1* | 12/2004 | Novak et al. | 707/200 |
| 2005/0015391 A1* | 1/2005 | Pohlan | 707/100 |
| 2005/0033773 A1* | 2/2005 | Roberge et al. | 707/104.1 |
| 2005/0125730 A1* | 6/2005 | Goddard et al. | 715/531 |
| 2005/0125781 A1* | 6/2005 | Swamy et al. | 717/144 |
| 2005/0246314 A1* | 11/2005 | Eder | 707/1 |
| 2007/0110047 A1* | 5/2007 | Kim | 370/389 |

FOREIGN PATENT DOCUMENTS

| | | |
|---|---|---|
| JP | 2000-181972 | 6/2000 |
| JP | 2002-236692 | 8/2002 |
| JP | 2005-031719 | 2/2005 |
| JP | 2005-251091 | 9/2005 |

\* cited by examiner

F I G . 6
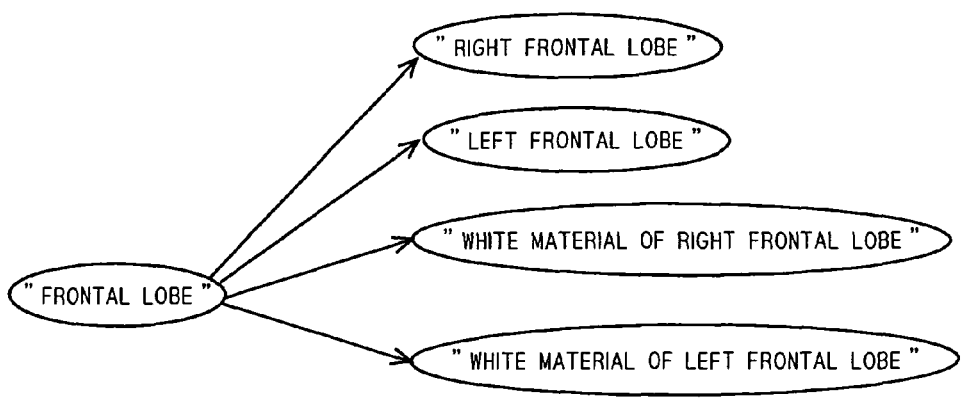
F I G . 7
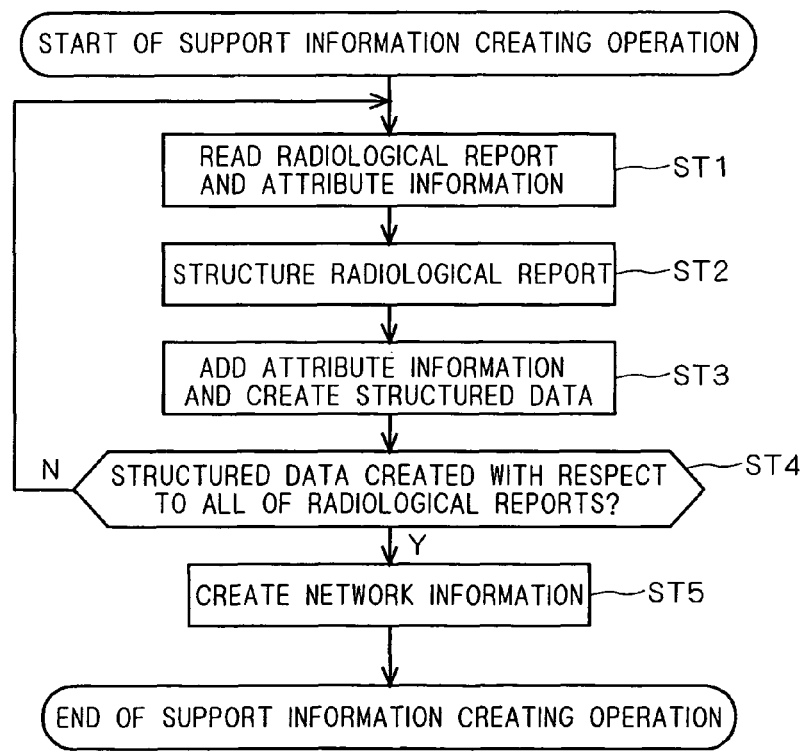

FIG. 10

| PATIENT LIST | | | |
|---|---|---|---|
| PATIENT NAME | SEX | EXAMINATION ID | STATUS |
| TARO TOKKYO | M | TOKKYO | UNDONE |
| ⋮ | | | |

FIG. 11

REQUEST

MALE, TWENTIES. HE COMES TO SEE A DOCTOR SINCE HE FORGETS THINGS MORE OFTEN. PLEASE CHECK BY MR ON THE HEAD.

FIG. 12

EXAMINATION INFORMATION

| ATTRIBUTES | VALUES |
|---|---|
| PATIENT ID | 593819-5 |
| PATIENT NAME | TARO TOKKYO |
| SEX OF PATIENT | MALE |
| BIRTHDAY | FEBRUARY, 2020 |
| EXAMINATION ID | TOKKYO |
| STATUS | UNDONE |
| DEGREE OF IMPORTANCE | IMPORTANT |
| ACCEPTANCE NO. | 234759 |
| REGION | SKULL |
| MODALITY | MRI |
| THE NUMBER OF IMAGES | 20 |
| IMAGE CAPTURE CONDITION | T2, FLAIR IMAGE |

FIG. 14
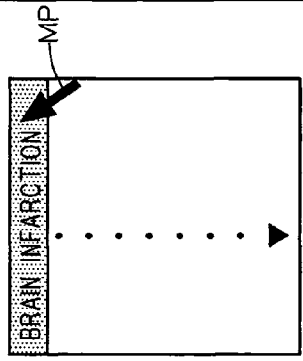
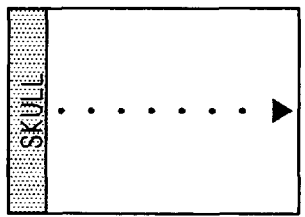
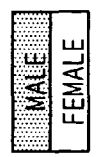

F I G . 1 5
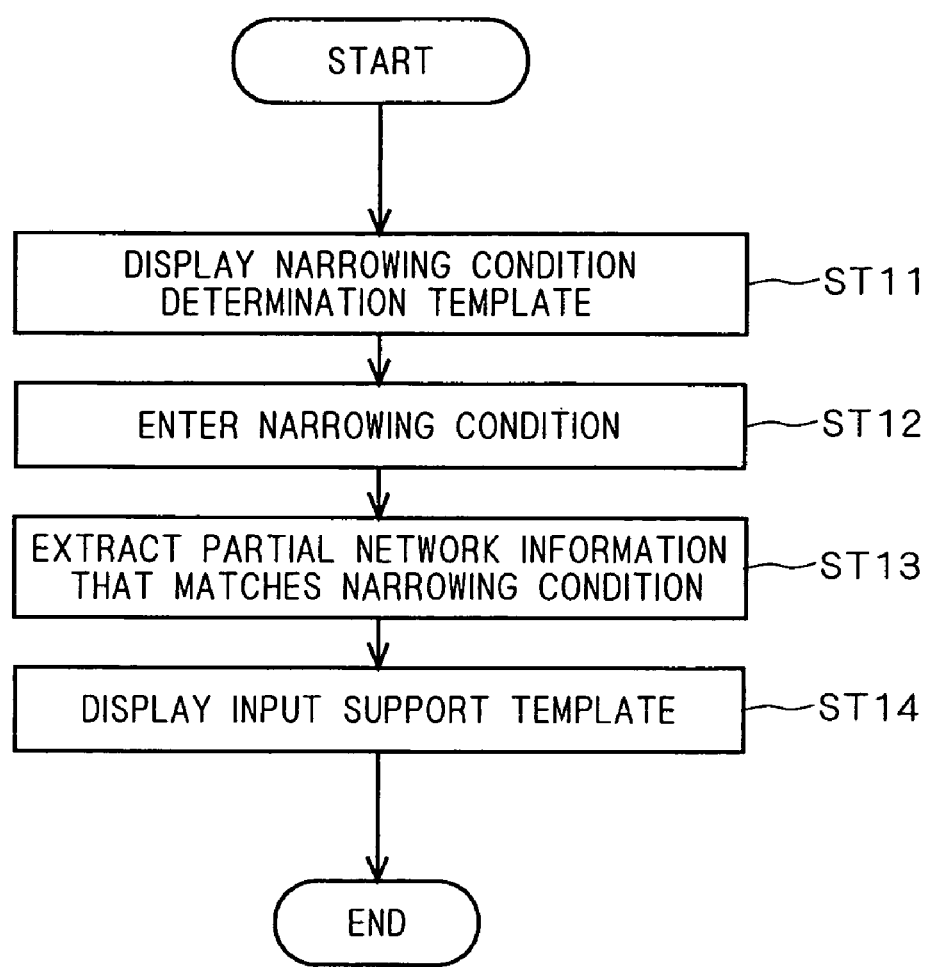

FIG. 16

| CATEGORY | IMAGE CAPTURE CONDITION | REGION | BASIC FINDINGS | DIAGNOSIS 1 | DIAGNOSIS 2 |
|---|---|---|---|---|---|
| BRAIN INFARCTION / ISCHEMIC CHANGE | T1 IMAGE / T2 IMAGE / FLAIR IMAGE / REFUSION IMAGE / T2 FLAIR IMAGE | FRONTAL LOBE / TEMPORAL LOBE / OCCIPITAL LOBE / PARIETAL LOBE / BASAL GANGLIA / NUCLEUS / THALAMUS / INTERNAL CAPSULE / EXTERNAL CAPSULE / BRAINSTEM / HYPOTHALAMUS / CEREBELLUM / MEDULLA OBLONGATE / PONS | POINT-LIKE AND/OR TACKETIC HIGH SIGNAL AREAS / POINT-LIKE HIGH SIGNAL AREAS / TACKETIC HIGH SIGNAL AREAS / HIGH SIGNAL AREAS / A NUMBER OF HIGH SIGNAL AREAS / DISPERSED HIGH SIGNAL AREAS | OLD BRAIN INFARCTION / WIDE-RANGED OLD BRAIN INFARCTION / SMALL OLD BRAIN INFARCTION / ACUTE BRAIN INFARCTION / WIDE-RANGED ACUTE BRAIN INFARCTION / SMALL ACUTE BRAIN INFARCTION / MALIGNANT ACUTE BRAIN INFARCTION / WIDE-RANGED MALIGNANT ACUTE BRAIN INFARCTION / SMALL MALIGNANT ACUTE BRAIN INFARCTION / BRAIN INFARCTION / WIDE-RANGED BRAIN INFARCTION / SMALL BRAIN INFARCTION / LACUNAR INFARCT / MULTIPLE BRAIN INFARCTION | THROMBOTIC INFARCT / EMBOLIC INFARCT / HEMORRHAGIC INFARCT / ANTERIOR CEREBRAL ARTERY INFARCTION / MIDDLE CEREBRAL ARTERY INFARCTION / POSTERIOR INFERIOR CEREBELLAR ARTERY INFARCTION / BASILAR ARTERY INFARCTION / ANTERIOR INFERIOR CEREBELLAR ARTERY INFARCTION / SUPERIOR CEREBELLAR ARTERY INFARCTION / THROMBOTIC INFARCT OF ANTERIOR CEREBRAL ARTERY / EMBOLIC INFARCT OF ANTERIOR CEREBRAL ARTERY / HEMORRHAGIC INFARCT OF ANTERIOR CEREBRAL ARTERY / THROMBOTIC INFARCT OF MIDDLE CEREBRAL ARTERY / EMBOLIC INFARCT OF MIDDLE CEREBRAL ARTERY |

VS: ● IS FOUND / ○ IS NOT FOUND.
W5 □ IS SUSPECTED.
W6 □ IS SUSPECTED.

SS: □ [FRONTAL LOBE]-[HIGH SIGNAL RANGE]-[FOUND]-[ACUTE BRAIN INFARCTION]-[ANTERIOR CEREBRAL ARTERY INFARCTION]

F I G . 1 8

INFORMATION PROCESSING SYSTEM

This application is based on application No. 2005-333181 filed in Japan, the contents of which are hereby incorporated by reference.

BACKGROUND OF THE INVENTION

1. Field of the Invention

The present invention relates to an information processing system.

2. Description of the Background Art

In the case of creating various reports by using knowledge accumulated in the past, conventionally, it is necessary to retrieve and refer to past reports by some method. In the case where a past report is structured by using a template or the like, it is unnecessary to refer to the full text of a retrieved report. However, the relation between reports and the like has to be found out with reference to an enormous amount of data.

For example, in the case of creating a so-called radiological report in a medical institution, when data is entered in a free format, abbreviations, expressions, and the like largely vary out of habit among doctors of radiology. Therefore, a report created by a doctor is not always friendly to the other doctors. At the time of creating a radiological report on the same symptom, it is difficult to create a radiological report with reference to radiological reports created by other doctors of radiology.

To address such a problem, a system has been proposed which supports simplification of creation of a radiological report by using a template in which words are selected from a pull-down menu for each of blanks of items (refer to Japanese Patent No. 3,212,957).

However, in the technique proposed in Japanese Patent No. 3,212,957, a doctor simply selects a word from a pull-down menu but cannot grasp the relation of words in items, such as a combination of words to be selected in the pull-down menus. Consequently, the past knowledge cannot be utilized. For example, a guideline for entry cannot be given on the basis of past knowledge. It is therefore difficult to create a radiological report accurately and smoothly. There is also a problem such that options to be selected are limited.

The problems are not limited to creation of medical reports. Such problems occur generally in various reports such as a sales report.

SUMMARY OF THE INVENTION

The present invention is directed to an information processing system.

According to the present invention, the information processing system includes: a first storage for storing an association information database in which association information is stored, the association information being information in which elements belonging to a plurality of element items in a one-to-one corresponding manner are associated with each other between the plurality of element items; an information extracting unit, in response to designation of an extraction condition of a user, for extracting partial association information corresponding to the extraction condition from the association information database; and a display for visibly outputting a view of network information in accordance with the partial association information, the network information being information in which a plurality of elements belonging to the plurality of element items are associated with each other between the plurality of element items so as to form a network.

Since the user can create a report while utilizing past knowledge with reference to the view, a technique for supporting accurate and smooth creation of a report can be provided.

According to another aspect of the present invention, the information processing system includes: a first storage for storing an association information database in which association information is stored, the association information being information in which elements belonging to a plurality of element items in a one-to-one corresponding manner are associated with each other between the plurality of element items; an information accepting unit for accepting input information in response to an input operation of a user, the input information being information corresponding to a combination of elements belonging to the plurality of element items in a one-to-one corresponding manner; an information updating unit for updating the association information database by adding information indicative of association of elements belonging to the plurality of element items in a one-to-one corresponding manner to the association information in accordance with the input information; and a display for visibly outputting a view of network information in accordance with the association information database, the network information being information in which a plurality of elements belonging to the plurality of element items are associated with each other between the plurality of element items so as to form a network.

Since creation of a report while effectively utilizing knowledge that changes with time can be supported by making the user refer to the view, a technique for supporting accurate and smooth creation of a report can be provided.

Therefore, an object of the present invention is to provide a technique for supporting accurate and smooth creation of a report.

These and other objects, features, aspects and advantages of the present invention will become more apparent from the following detailed description of the present invention when taken in conjunction with the accompanying drawings.

DESCRIPTION OF THE DRAWINGS

FIG. 6 is a diagram showing the relations between a major word or phrase and region phrases.

FIG. 7 is a flowchart showing the flow of operations of generating network information.

FIG. 10 is a diagram showing a display example of an examination list.

FIG. 11 is a diagram showing a display example of request information.

FIG. 12 is a diagram showing a display example of attribute information of a patient and an examination.

FIG. 14 is a diagram illustrating a display example of an extraction condition determination template.

FIG. 15 is a flowchart showing operations of narrowing information to be displayed.

FIG. 16 is a diagram showing a display example of an input support template.

FIG. 18 is a diagram illustrating a display element of a modification.

DESCRIPTION OF THE PREFERRED EMBODIMENTS

Embodiments of the present invention will be described hereinbelow with reference to the drawings.

Outline of Information Processing System

Figure 1:
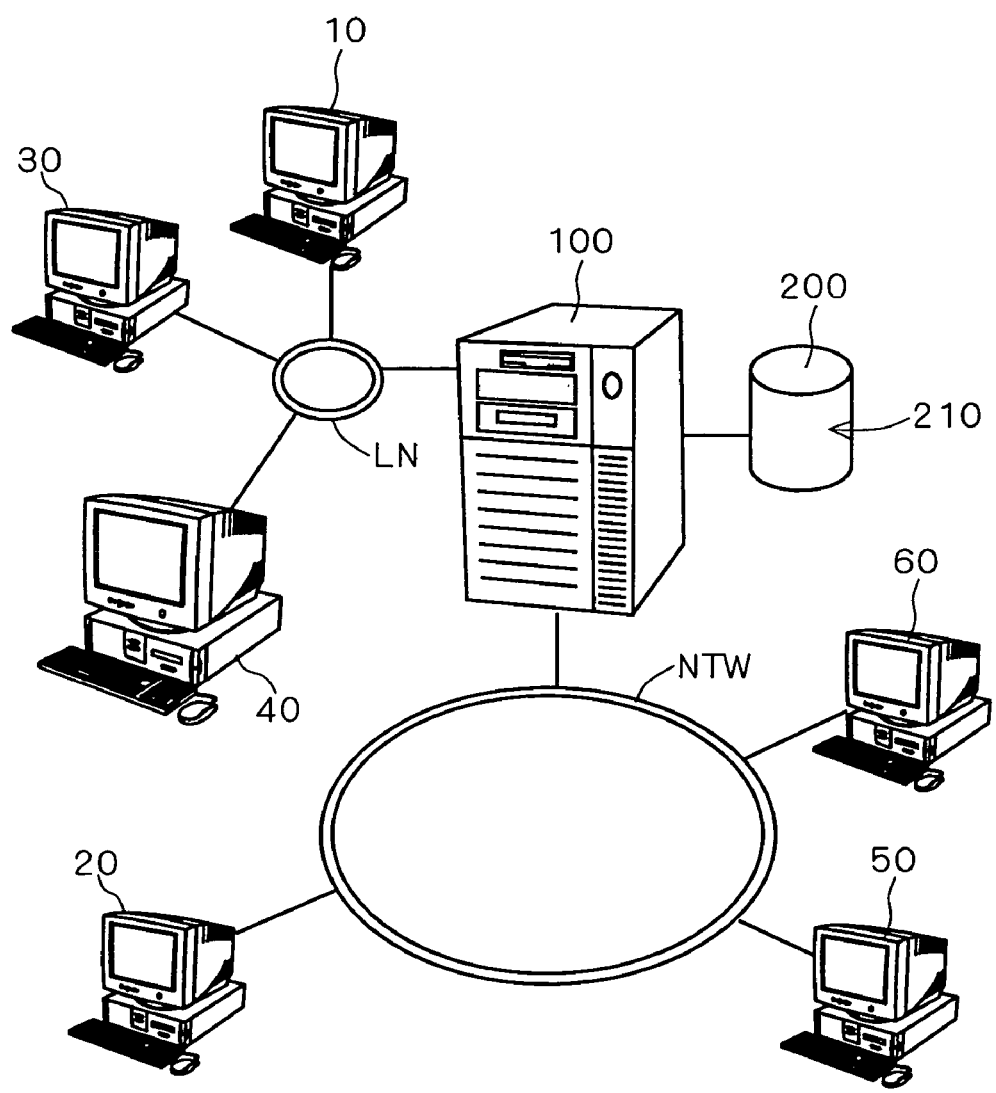
FIG. 1 is a diagram showing an outline of an information processing system according to the present invention.

FIG. 1 is a diagram showing an outline of an information processing system 1 according to an embodiment of the invention.

The information processing system 1 is, for example, a system for controlling and processing diagnosis information in a hospital. In the system 1, a server 100 and terminals 20, 50, and 60 are connected to a network circuit NTW such as LAN so as to transmit/receive data to/from each other. To the server 100, a storage 200 is connected so that data can be transmitted/received and, further, the terminals 10, 30, and 40 are connected via a network line LN so that data can be transmitted/received.

The storage 200 stores a diagnosis information database (DB) 210 for storing medical information (hereinbelow, also called "diagnosis information") of a number of patients to be diagnosed. The diagnosis information DB 210 includes data indicative of a list of a number of patients to be diagnosed (a patient list).

In the diagnosis information DB 210, a number of pieces of image data obtained by image capturing with a radiation ray in a department of radiology on patients in the patient list, and report data indicative of radiological reports corresponding to the number of pieces of image data are stored so as to be associated with the names of the patients in the patient list. When attention is paid to a point that a number of pieces of report data are stored, the diagnosis information DB 210 is a database (report DB) in which a number of pieces of report data are stored.

In the diagnosis information DB 210, attribute information indicative of information of requests from primary doctors, patients and examinations is stored so as to be associated with the names of patients in the patient list.

The server 100 writes/reads various information to/from the diagnosis information DB 210 and performs an information process based on various information stored in the diagnosis information DB 210. The various information in the server 100 is properly controlled by the terminal (control client) 10.

In the information processing system 1, for example, the terminals 50 and 60 are terminals used by primary doctors of patients, the terminal 40 is a terminal (input client) to which report data indicative of a radiological report is input by a reading physician of a radiology department, and the terminal 30 is a terminal used by an X-ray technologist of the radiology department. When a request is entered from the terminals 50 and 60 to the terminal 30 of the radiology department, the X-ray technologist of the radiology department obtains image data of an affected area by MRI, CT, or the like, and image data of the affected area is stored from the terminal 30 to the diagnosis information DB 210 via the server 100. After that, the doctor of the radiology department enters report data indicative of the radiological report in the input client 40 with reference to a screen on which image data to be stored in the diagnosis information DB 210 is visibly output. Although the control client 10 and the input client 40 are constructed by different terminals in this embodiment, they may be constructed by a single terminal having the functions of the clients.

The server 100 generates information (input support information) for supporting an entry of report data indicative of a new radiological report by using report data indicative of radiological reports (existing radiological reports) already stored in the diagnosis information DB 210, extracts necessary information from the input support information, and provides the extracted information in the form of a template to the terminal 40. The function of supporting an entry of report data indicative of a new radiological report in the server 100 will be also called an "input support function" (which will be described later).

Figure 2:
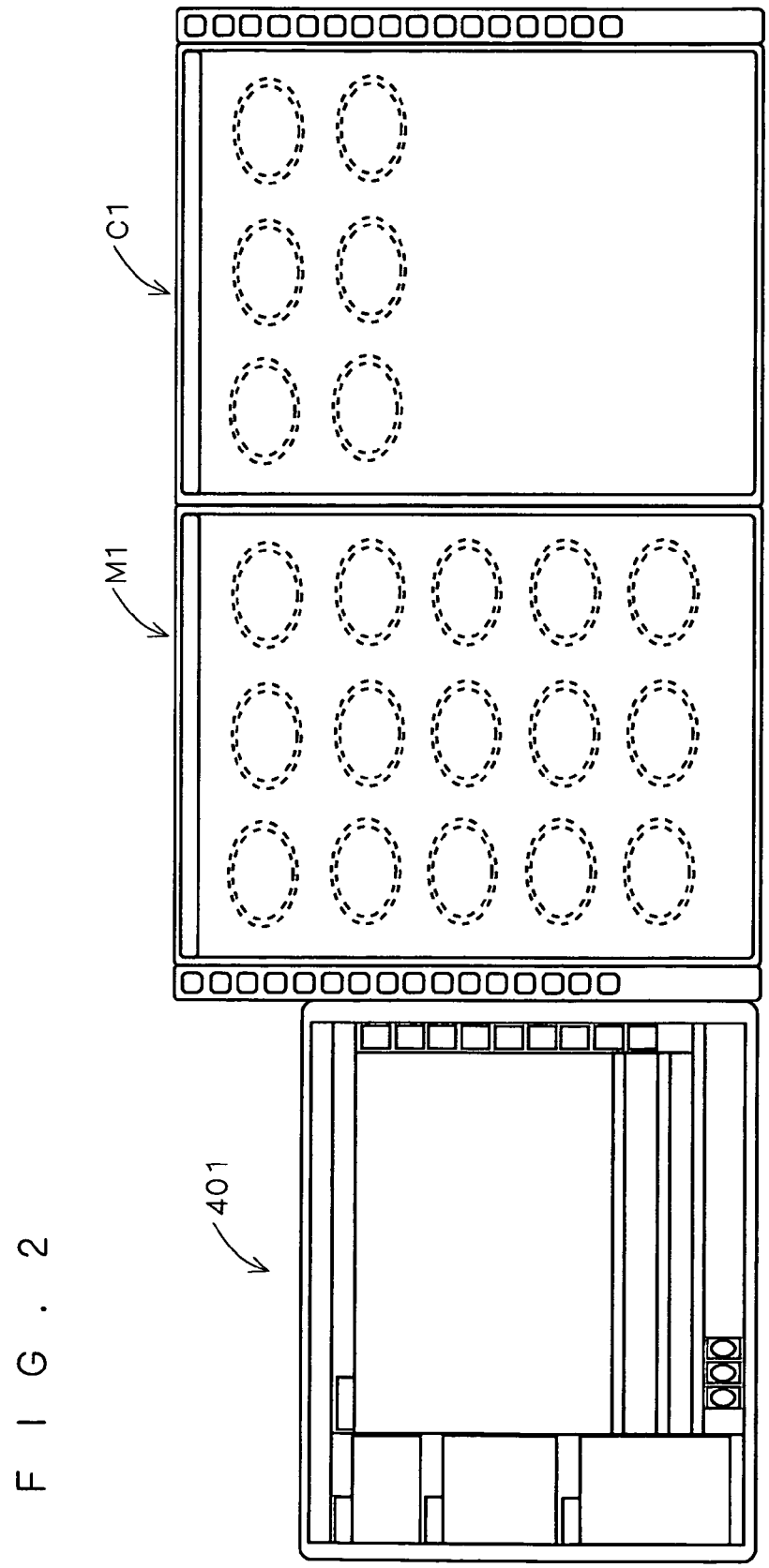
FIG. 2 is a diagram illustrating a state of entering a radiological report.

FIG. 2 is a diagram illustrating a state where report data indicative of a new radiological report is entered in the input client 40. As shown in FIG. 2, in the input client 40, a reading physician in the radiology department enters report data indicative of a new radiological report on a radiological report input screen 401 by properly referring to screens (image display screens) M1 and C1 on which image data of a patient stored in the diagnosis information DB 210 is visibly output.

Input Support Function

The input support function is a function of creating input support information by extracting elements necessary for entering report data indicative of a new radiological report from report data indicative of a number of radiological reports stored in the diagnosis information DB 210 as past knowledge, and structuring the elements by using the RDF (Resource Description Framework) or the like, and properly presenting the created input support information.

The input support function of the information processing system 1 will be described hereinbelow.

Figure 3:
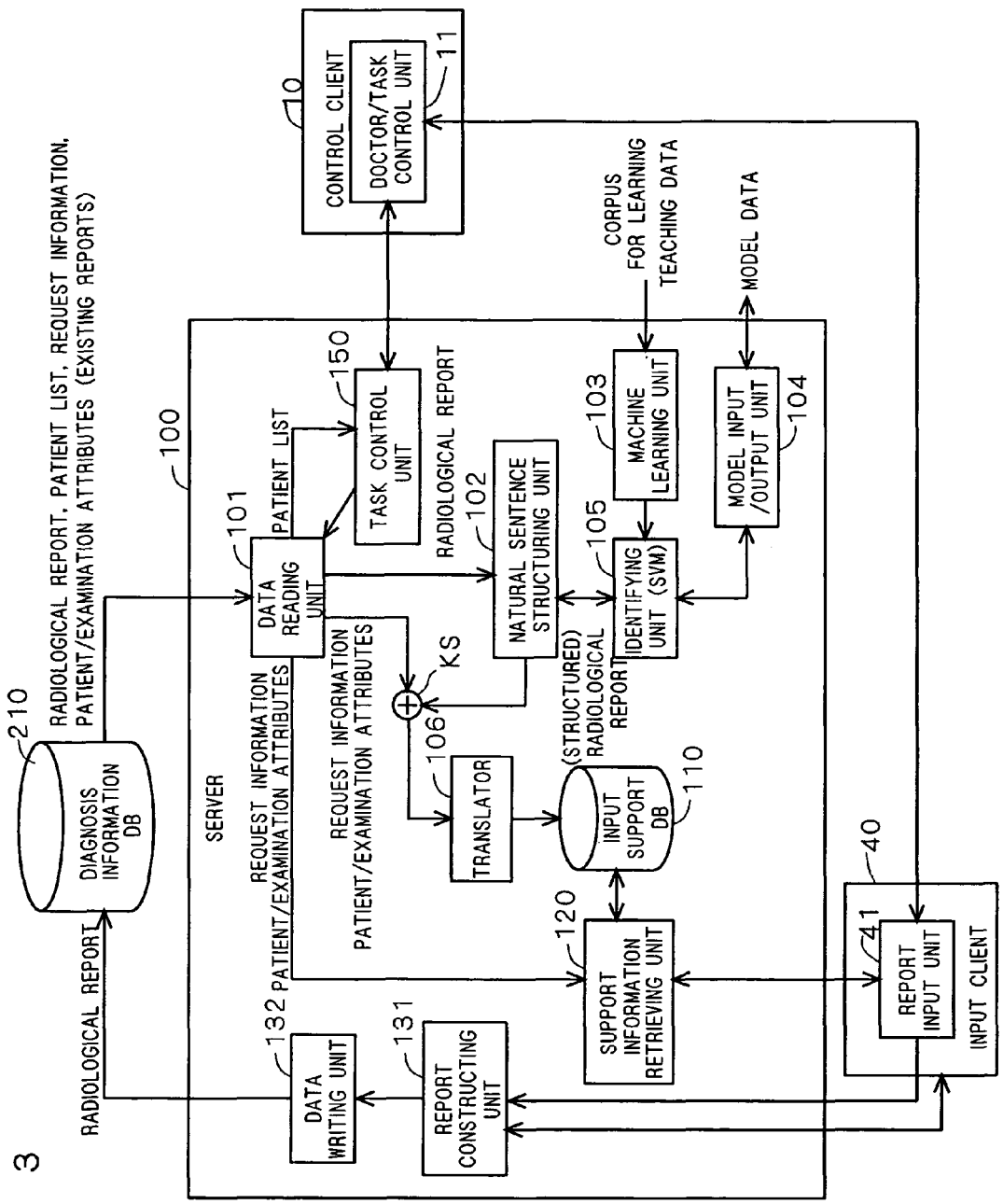
FIG. 3 is a block diagram showing a functional configuration related to an input support function.

FIG. 3 is a block diagram showing a functional configuration regarding the input support function and entry of report data indicative of a new radiological report by using the input support function in the information processing system 1. The functional configuration shown in FIG. 3 is realized by executing a program stored in a storage such as a hard disk by a CPU or the like in each one of the server 100, the input client 40, and the control client 10. Various data temporarily stored in various information processes executed by the functional configuration is temporarily stored in a RAM or the like provided in each one of the server 100, input client 40, and control client 10.

Operations realized by the input support function are mainly three operations; an operation (support information creating operation) for generating input support information, an operation (patient specifying operation) for specifying a patient corresponding to report data indicative of a new radiological report to be entered, and an operation (input supporting operation) for actually supporting entry of report data indicative of a new radiological report on the basis of the input support information.

The support information creating operation, the patient specifying operation, and input supporting operation will be described one by one hereinbelow with reference to FIG. 3.

Support Information Creating Operation

A data reading unit 101 reads from the diagnosis information DB 210, information indicative of existing radiological reports (existing report information), and information related to requests, patient's attributes, and examination attributes corresponding to the existing report information. The data reading unit 101 transmits the existing report information to a natural sentence structuring unit 102, and transmits the information related to the requests, patient's attributes, and examination attributes to an information adder KS.

The natural sentence structuring unit 102 extracts necessary elements from a sentence of a findings as a natural sentence of the existing radiological report and structures the elements by using the RDF. The structuring of the elements derived from the existing radiological report is realized by the functions of a machine learning unit 103, a model input/output unit 104, and an identifying unit 105 and the function of the natural sentence structuring unit 102.

The machine learning unit 103 learns, for example, information as a reference of structuring when a corpus for learning or the like is given as teaching data.

The corpus for learning includes a large amount of text data according to the format (sentence model) of the sentence of the findings of the radiological report. The sentence model shows the configuration of the sentence of the findings of the radiological report such as "image capture conditions"-"region"-"basic findings ("feature"-"conclusive words")"-"diagnosis 1 ("diagnosis"-"conclusive words")"-"diagnosis 2("diagnosis"-"conclusive words")". In the corpus for learning, for example, classification item names of the elements constructing the sentence model of the sentence of the findings included in a model of a radiological report (also called "report model") are tagged to words.

Examples of the element classification items are "category of a diagnosis (hereinbelow, called "category"), "image capture condition", "region", "basic findings", "general diagnosis (hereinbelow, called "diagnosis 1"), and "detailed diagnosis (hereinbelow, called "diagnosis 2").

In the corpus for learning, for example, the classification item name "category" of an element is tagged to each of words or phrases such as "brain infarction" and "ischemic change". The element classification item name "image capture condition" is tagged to each of words or phrases such as "T1 image" and "T2 image". The element classification item name "region" is tagged to each of words or phrases such as "frontal lobe" and "temporal lobe". The element classification item name "basic findings" is tagged to each of words or phrases such as "point-like and/or tachetic high signal are" and "point-like high signal area". The element classification item name "diagnosis 1" is tagged to each of words or phrases such as "old brain infarction" and "wide-ranged old brain infarction", and the element classification item name "diagnosis 2" is tagged to each of words or phrases "thrombotic infarct" and "embolic infarct".

When such a corpus for learning is given from the outside to the machine learning unit 103, to create a new radiological report which will be described later, representative expressions of conclusive words or phrases are also similarly tagged in the corpus for learning.

The machine learning unit 103 extracts a word or a phrase from the corpus for learning and stores it in a corresponding element classification item. Specifically, the machine learning unit 103 uses teaching data including the corpus for learning as learning materials, and learns and stores a word or a phrase belonging to each of the element classification items with reference to the teaching data. In this operation, the machine learning unit 103 normalizes variations of words or phrases and expressions to some extent.

Further, the machine learning unit 103 also learns and stores an element appearing pattern in the corpus for learning. For example, the machine learning unit 103 learns and stores an appearing pattern indicating the appearing order of words or phrases belonging to respective classification items such that a word or a phrase belonging to "basic findings" appears after the region "frontal lobe".

In the machine learning unit 103, the data learnt and stored is used as data of a model (model data) indicative of decomposition of elements constructing an existing radiological report to element classification items.

The model input/output unit 104 outputs the model data to an external computer via a communication line, a storing medium, or the like and inputs the model data learnt by an external computer via a communication line, a storing medium, or the like. Therefore, the model data learnt by the information processing system 1 can be used by another information processing system. On the contrary, model data learnt by another information processing system can be used by the information processing system 1.

The identifying unit 105 identifies an element classification item and an actually used word or phrase in an existing radiological report input to the natural sentence structuring unit 102 while using model data learnt by the machine learning unit 103 or model data obtained via the model input/output unit 104.

By using the above-described machine learning method, the element classification items of only elements (in the embodiment, words or phrases) listed in the teaching data can be identified. However, by using the following machine learning method, the element classification items of also elements which are not preliminarily listed in the teaching data can be identified.

For example, the machine learning unit 103 disassembles the corpus for learning into morphemes by a morphological analysis and learns, for each of morphemes, a pattern in which a morpheme belonging to a certain classification item appears by using information such as the morpheme itself, the word class of the morpheme, the inflected forms of the morpheme, and preceding and subsequent morphemes (for example, preceding two morphemes and subsequent two morphemes). The identifying unit 105 can recognizes the element classification item of also an element (in this case, a word or a phrase) which has not been preliminarily given in accordance with the pattern.

More concretely, for example, in the case where a sentence such as "along " (various words or phrases can be used for the part "") frequently appears in the corpus for learning and a word or a phrase indicative of a region frequently appears in the part "", the machine learning unit 103 can learn a pattern that a word or a phrase indicative of a region enters in the part "". By using such a pattern, the identifying unit 105 can extract "pituitary gland" as a word or a phrase indicative of a region from the phrase "along the pituitary gland" from the relations among words or phrases. The machine learning can be realized by using so-called SVM (Support Vector Machine). By such machine learning, the precision of the natural language processing improves.

The natural sentence structuring unit 102 structures report data indicative of existing radiological reports by disassembling the existing radiological reports into words or phrases (elements) belonging to the respective element classification items and describing the words or phrases in the RDF language. At this time, an element appearing pattern in the existing radiological reports can be also recognized. Therefore, by making information related to the appearing pattern reflected in the model data used by the identifying unit 105, the model data can be improved. That is, the more the existing radiological reports are analyzed, the more the model data can be improved.

A piece of report data indicative of an existing radiological report structured by the natural sentence structuring unit 102 is output to the information adder KS in which the attribute information of the request, the patient's attributes, and the examination attributes sent from the data reading unit 101 is added, thereby creating structured data described in the RDF language.

Figure 4:
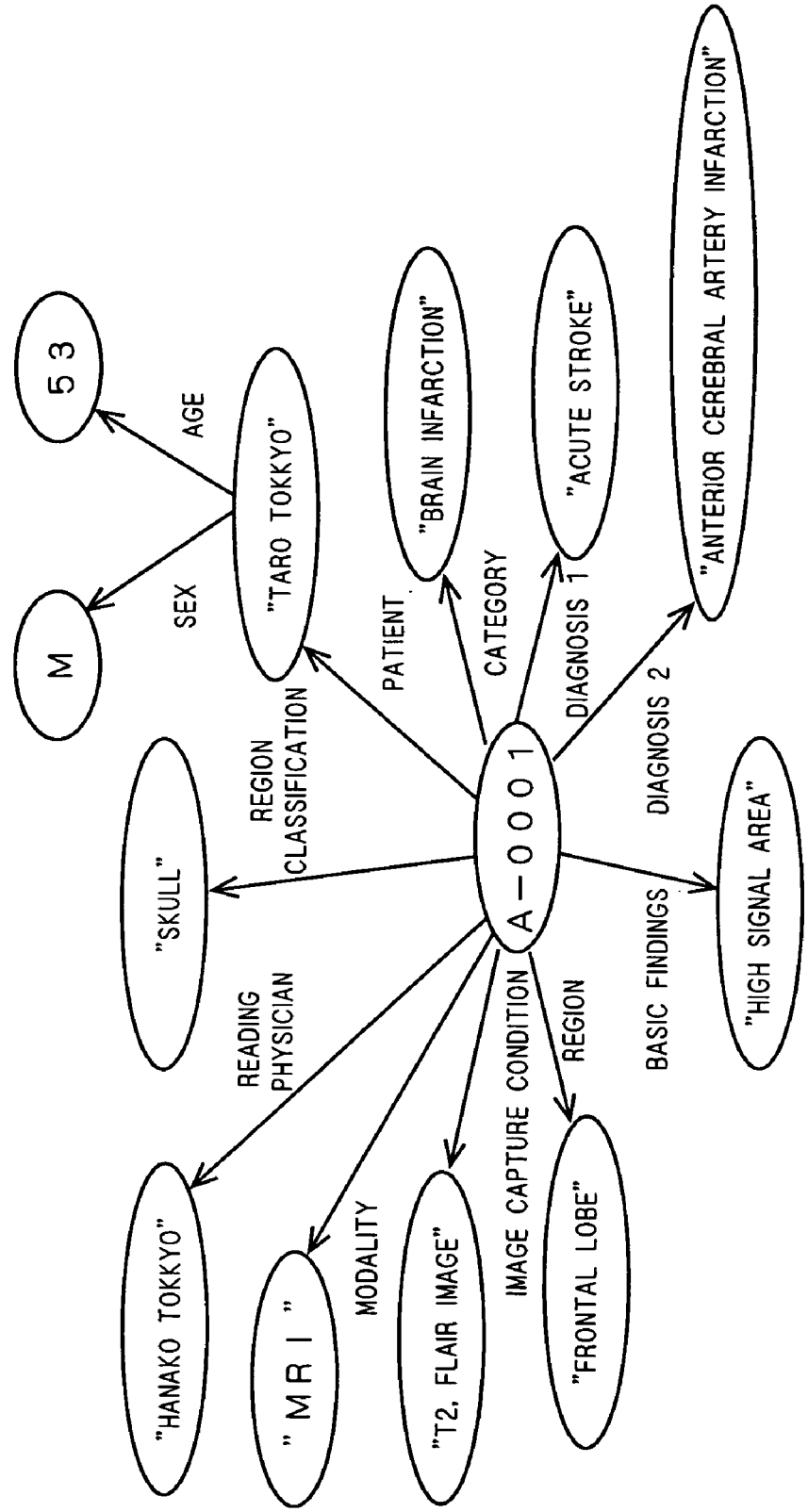
FIG. 4 is a diagram showing an example in which elements related to a radiological report are structured.

FIG. 4 is a diagram illustrating data (hereinbelow, called "single report structured data") obtained by structuring elements of a single existing radiological report (including elements constructing the attribute information of the existing radiological report). As shown in FIG. 4, for a file "A-0001" of report data indicative of an existing radiological report, attributes values "brain infarction", "T2, flair image", "frontal lobe", "high signal area", "acute stroke", and "anterior cerebral artery infarction" are described so as to be associated with, as attribute items, the element classification items "category", "image capture condition", "region", basic findings", "diagnosis 1", and "diagnosis 2", respectively. For attribute items of the attribute information, which are "region classification", "patient", "reading physician", and "modality", "skull", "Taro Tokkyo", "Hanako Tokkyo", and "MRI" are associated. Further, for the attribute items "sex" and "age" with respect to the attributes of the patient, "M" and "53" are associated, respectively. The attribute items to be associated in the single report structured data are not limited to those shown in FIG. 4 but other attribute items included in, for example, information of examination attributes may be included.

Such single report structured data is created for each of a number of pieces of existing report information stored in the diagnosis information DB 210 by the functions of the natural sentence structuring unit 102, the machine learning unit 103, the model input/output unit 104, the identifying unit 105, and the information adder KS. The created data is output to a translator 106.

In the translator 106, a process of arranging a plurality of attribute values associated to one file in each single report structured data by attribute items, re-associating the attribute values, and describing the attribute values in the RDF language is performed on all of a number of pieces of single report structured data. As a result of the process, a plurality of attribute values (in this case, words or phrases) are listed by attribute items included in a plurality of attribute items, and information in which the attribute values are associated with each other between the attribute items so as to form a network (hereinbelow, also called "network information") is created. By storing the network information in a predetermined storage, the network information is used as input support information for supporting an input of report data indicative of a radiological report, and a database (input support DB) 110 is configured.

Figure 5:
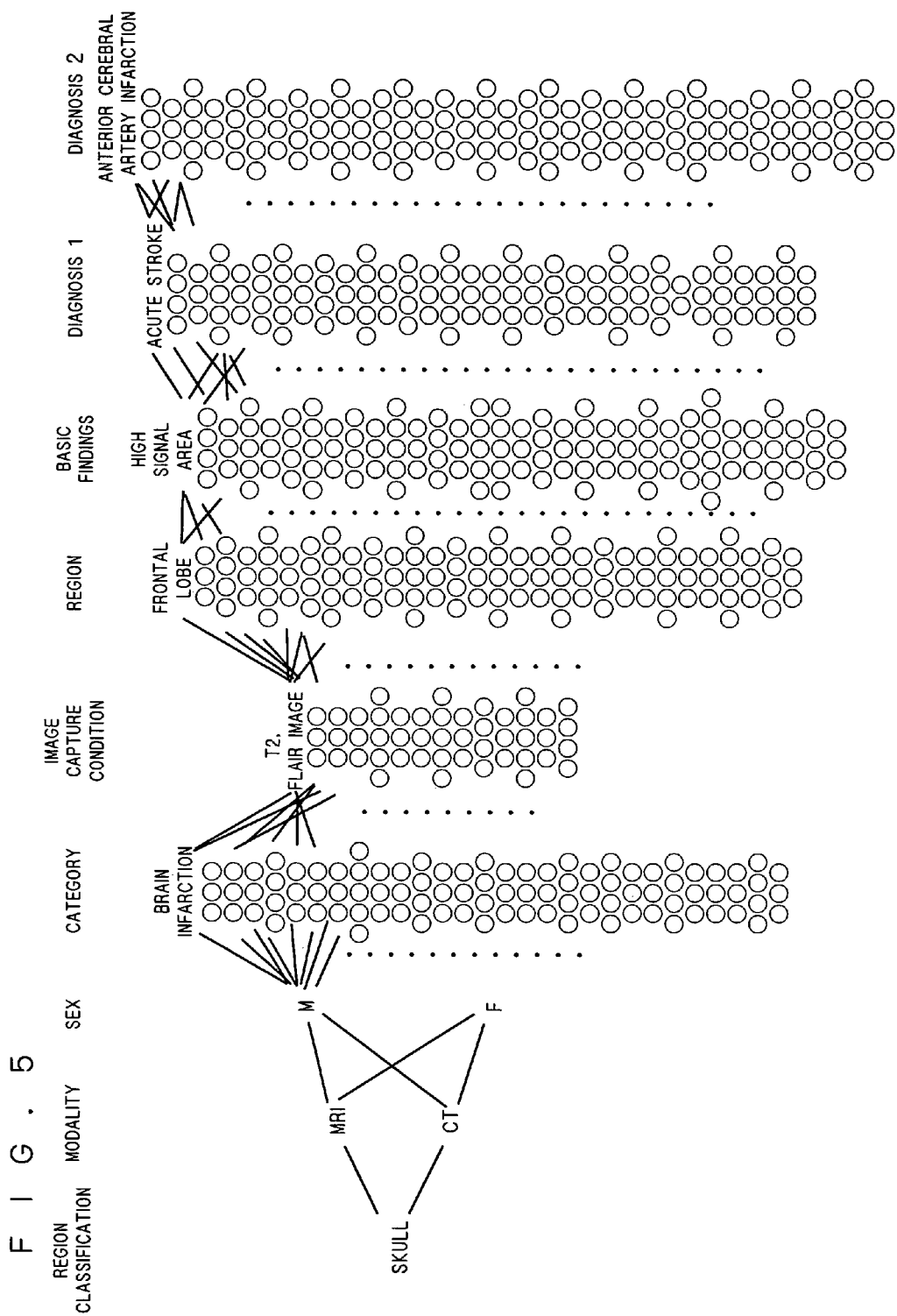
FIG. 5 is a diagram showing an example in which elements related to a number of radiological reports are structured.

FIG. 5 is a diagram showing an example in which elements of a number of existing radiological reports are structured, and illustrates network information on the region classification "skull". In FIG. 5, associated words or phrases are connected via lines. In FIG. 5, to avoid complication of the drawing, words are illustrated as "OOO" and the like and, as lines indicative of association, only lines which are positioned in an upper part in the diagram are illustrated and the other lines are omitted.

At the time of creating network information by the translator 106, the number of combinations of words or phrases between the items in each single report structured data is counted, and the count information is stored in the input support DB 110. For example, the number of combinations of words or phrases such as "skull, MRI, M, brain infarction, T2 flair image, frontal lobe, high signal area, acute stroke, and anterior cerebral artery infarction" is stored as count information.

The network information and the count information is information indicative of association among a plurality of words or phrases belonging to respective items, so that it will be properly generically called "association information".

In the network information stored in the input support DB 110, association of a plurality of words or phrases in an existing radiological reports among the attribute items is shown. Consequently, it is effective to output the network information in a visible form and use it at the time of inputting report data indicative of a new radiological report. In particular, it is effective to provide the network information in the form of a template in which the attribute items are set as input element items and a plurality of words or phrases listed in the attribute items are set as input candidates (options).

However, in the network information stored in the input support DB 110, when there are too may synonyms (for example, "T2 emphasized image", "T2 W1", and the like) for any of the words or phrases listed in the attribute items, options are too many and it is difficult to designate an option. Consequently, at the time of detecting a word or a phrase, the identifying unit 105 performs a process of replacing synonyms with a single representative word or a phrase. In the case where "conclusive words or phrases" or the like exist in the attribute items, when the expressions of conclusive words or phrases or the like vary largely (for example, "is considered" and "will be considered"), the number of options is too large, and it is difficult to designate an option. With respect to variations in expression, at the time of detecting conclusive words or phrases, the identifying unit 105 performs a process of replacing words or phrases to one representative expression.

Such replacement of words or phrases to one representative word or phrase can be realized by including a table in which a plurality of words or phrases and a representative word or phrase are associated with each other in the teaching data. With respect to the variations in expression, the variations may be normalized and replaced with the word or phrase of the highest use frequency. Synonyms may be also replaced with a synonym of the highest use frequency.

In a radiological report, as the attribute item "region", a phrase (region phrase) in which a major word or phrase, a minor word or phrase, a prefix, and a suffix are combined is often used. For example, the region phrase "white matter in the right frontal lobe" is combination of the major phrase "frontal lobe", the minor phrase "white material", and the prefix "right". Since the region phrases are constructed by a number of combinations of the major word or phrase, minor word or phrase, prefix, and suffix, the number of options is too large, and it is difficult to designate an option. Consequently, with respect to the attribute item "region", the region phrase is disassembled. In the network information, major words or phrases of the attribute item "region" are listed. Besides the network information, as shown in FIG. 6, the region phrases are associated with each of the major words or phrases.

FIG. 7 is a flowchart showing the flow of operations of creating input support information. The operation flow is realized by executing the program for realizing the input support function in the server 100.

In step ST1, the data reading unit 101 reads data indicative of a radiological report together with attribute information from the diagnosis information DB 210.

In step ST2, the data indicative of a radiological report is structured by the functions of the natural sentence structuring unit 102, the machine learning unit 103, the model input/output unit 104, and the identifying unit 105.

In step ST3, by the function of the information adder KS, the attribute information is added to the data indicative of the structured radiological report. As a result, single report structured data as shown in FIG. 4 is created.

In step ST4, whether single report structured data has been created with respect to report data indicative of all of radiological reports stored in the diagnosis information DB 210 or not is determined. In the case where single report structured data has not been created with respect to report data indicative of all of radiological reports, data indicative of the next radiological report or the like is read, and single report structured data is created. In the case where single report structured data has been creased with respect to the report data indicative of all of the radiological reports, the program advances to step ST5.

In step ST5, network information is created on the basis of the single report structured data on all of the radiological reports, and the operation flow is finished.

The number of pieces of report data indicative of radiological reports stored in the diagnosis information DB 210 increases each time a piece of report data indicative of a new radiological report is created in accordance with an input from the input client 40. It is effective when report data indicative of radiological reports being stored with time can be also used as past knowledge. In particular, in the case where data indicative of new findings are included in a piece of newly stored radiological report data, the past knowledge is further enriched, so that it is more effective.

For example, by executing an operation flow similar to the network information creating operation flow shown in FIG. 7 each time data indicative of a new radiological report is written to the diagnosis information DB 210 from a data writing unit 132, the network information is updated to network information in which the new radiological report is reflected.

Figure 8:
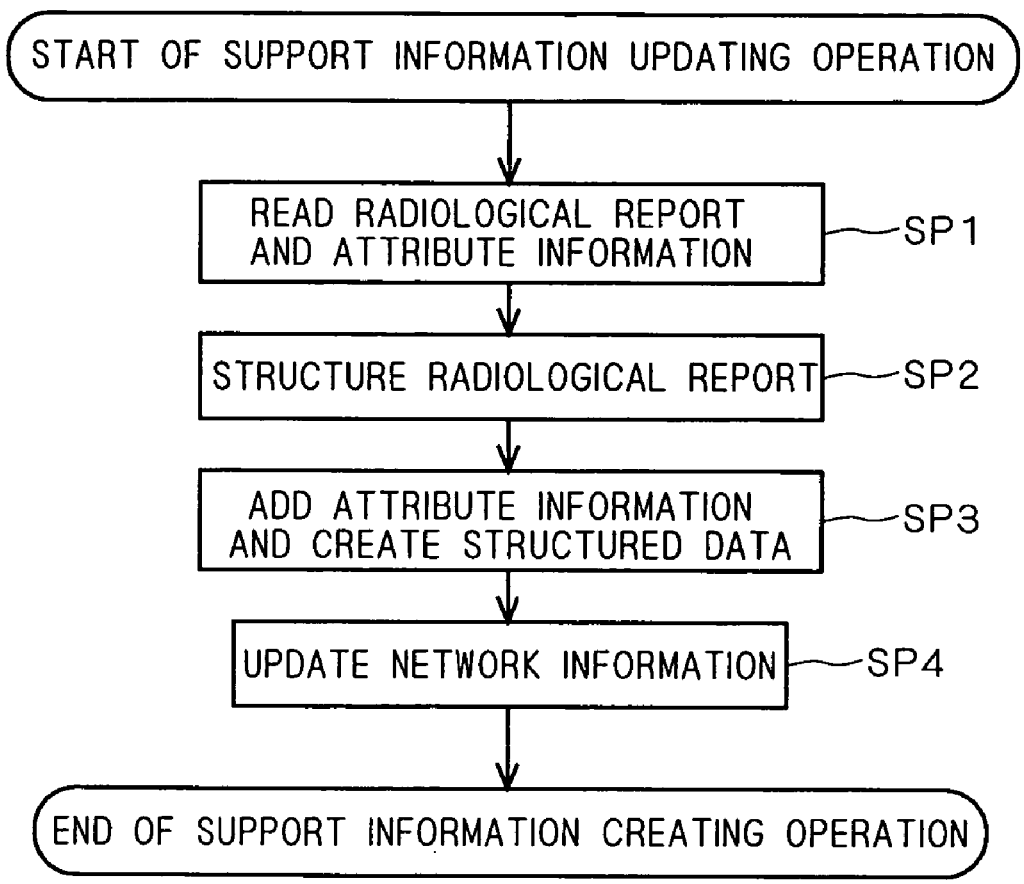
FIG. 8 is a flowchart showing the flow of operations of updating network information.

FIG. 8 is a flowchart showing a network information updating operation flow. The operation flow is realized by executing the program for realizing the input support function in the server 100.

In step SP1, in response to an input operation of the user, data indicative of a new radiological report which is added from the data writing unit 132 to the diagnosis information DB 210 is read together with the attribute information.

In step SP2, the data indicative of the radiological report read in step SP1 is structured by the functions of the natural sentence structuring unit 102, machine learning unit 103, model input/output unit 104, and identifying unit 105.

In step SP3, by the function of the information adder KS, attribute information is added to the data indicative of the structured radiological report, thereby creating single report structured data as shown in FIG. 4.

In step SP4, by the translator 106, on the basis of the structured data generated in step SP3, information indicative of the relation among words or phrases belonging to the different attribute items with respect to the new radiological report is added to the network information already stored in the input support DB 110, thereby updating the network information. Obviously, the information indicative of the number of times stored as the count information is also updated at this time.

Patient Specifying Operation

Next, a patient specifying operation realized by the input support function in the case of displaying a screen for inputting report data indicative of a new radiological report (radiological report input screen) and allowing report data indicative of a new radiological report to be entered in the input client 40 will be described.

The data reading unit 101 reads data indicative of a patient list (patient list data) from the diagnosis information DB 210 and transfers it to a task control unit 150. The task control unit 150 provides patient list data via the control client 10 to the input client 40. In the input client 40, the patient list is displayed on the radiological report input screen.

Figure 9:
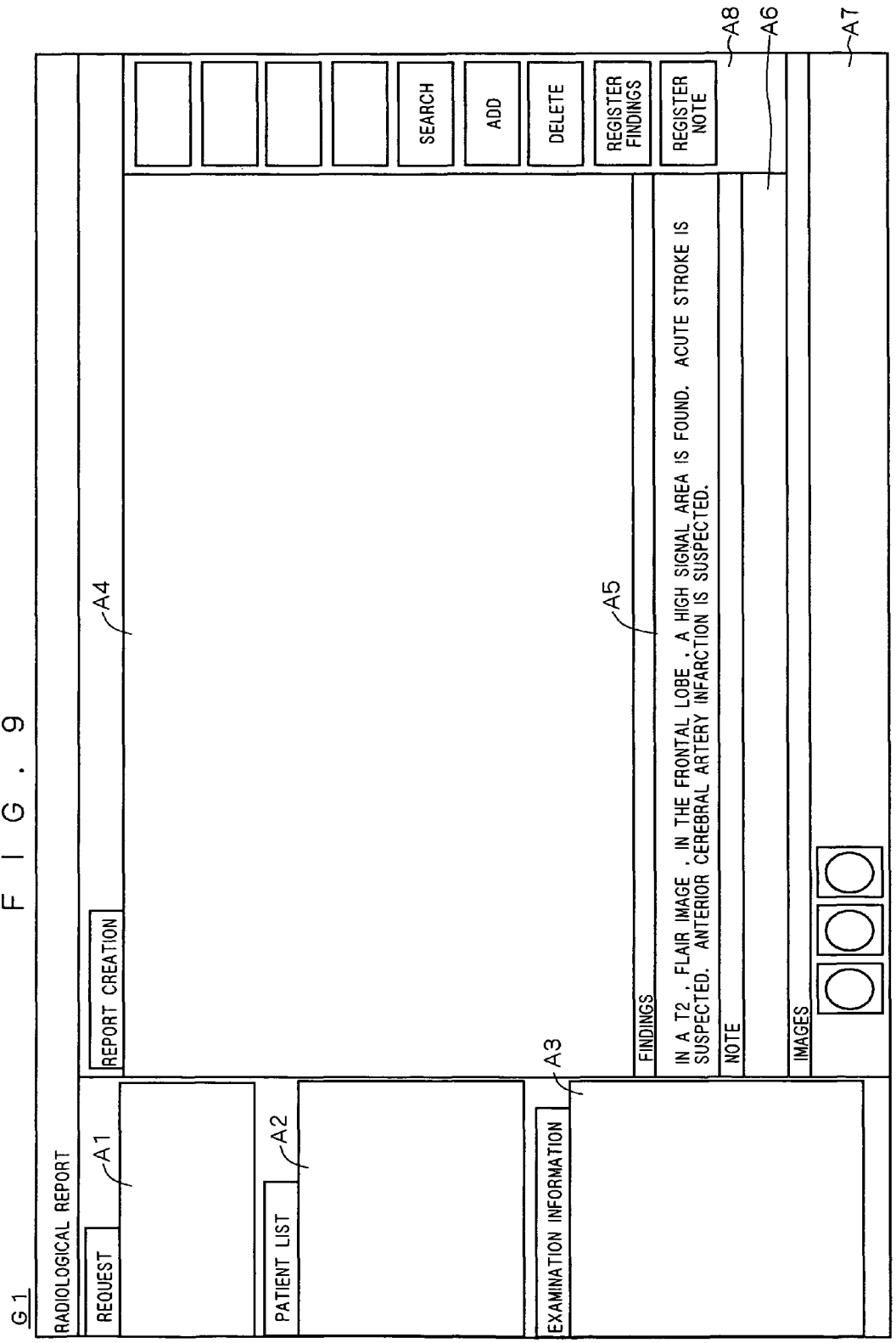
FIG. 9 is a diagram illustrating a radiological report input screen.

FIG. 9 is a diagram illustrating a radiological report input screen G1. As shown in FIG. 9, the radiological report input screen G1 is constructed by, mainly, an area (request display area) A1 in which a request (ordering information) is displayed, an area (patient list display area) A2 in which the patient list is displayed, an area (examination information display area) A3 in which examination information is displayed, an area (report creating area) A4 used for inputting and creating report data indicative of a radiological report, an area (findings display area) A5 in which findings are displayed, an area (memo area) A6 serving as a memo, an area (image attaching area) A7 for attaching a representative image, and an area (command input area) A8 in which icons for entering commands are listed.

In the input client 40, in the patient list display area A2 in the radiological report input screen G1, for example, an patient list as shown in FIG. 10 is displayed. In the patient list, the names of patients are listed in order from above, and the sex, examination ID, and a status showing whether report data indicative of a radiological report has been created or not are written for each of the names of the patients.

Therefore, a reading physician can designate a desired patient from the patient list by properly operating a mouse or the like of the input client 40 in a state where the patient list is displayed in the patient list display area A2. The information indicative of the designated patient name is output to the task control unit 150 by the function of a doctor/task control unit 11 in a control client 10. The task control unit 150 specifies a task for creating report data indicative of a new radiological report corresponding to the designated patient name.

Under control of the task control unit 150, the data reading unit 101 reads the information of the request, the patient attributes and examination attributes corresponding to the designated patient name from the diagnosis information DB 210. The read information of the request, the patient attributes and examination attributes is provided for the input client 40 via a support information retrieving unit 120. On the basis of the provided information of the request, the patient attributes and examination attributes, request information as shown in FIG. 11 is displayed in the request information display area A1, and the attribution information of the patient attributes and the examination attributes as shown in FIG. 12 is displayed in the examination information display area A3.

Input Support Operation

In the input support operation, the network information created as described above is visibly output in the form of a template in the report creating area A4, options of words or phrases in the template display are properly designated, thereby inputting report data indicative of a new radiological report.

When a plurality of words or phrases listed in the attribute items are used as options and all of the network information (whole network information) is simply provided in the form of a template showing a view as shown in FIG. 5, the number of options listed is too large, and it is difficult to choose an option.

Figure 13:
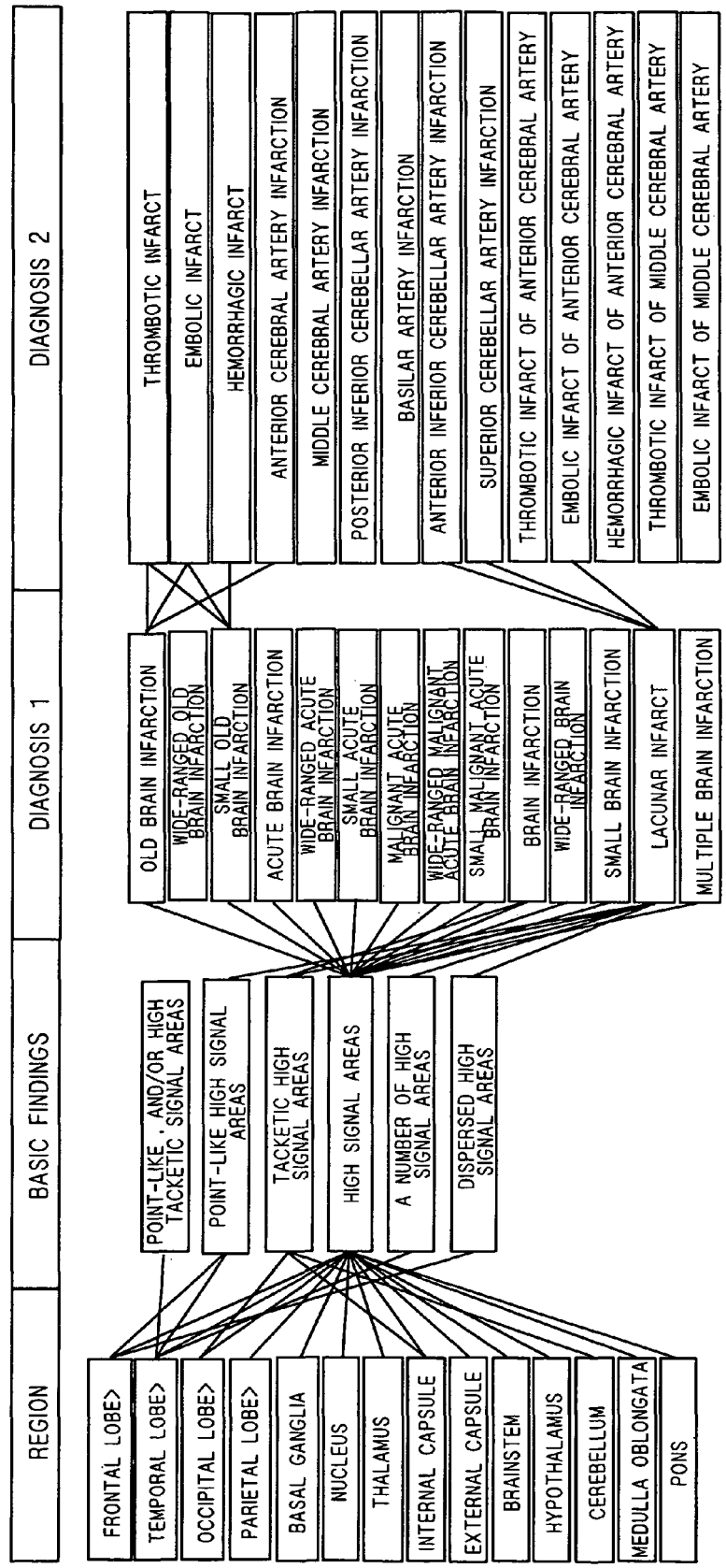
FIG. 13 is a diagram illustrating a structure of partial network information.

For example, when the whole network information is narrowed to information related to "male, skull, MRI, brain infarction", for example, a part of the network information (partial network information) as shown in FIG. 13 can be extracted. The partial network information shown in FIG. 13 is information in which a plurality of options belonging to the input element items are associated with each other so as to form a network between the input element items "region", "basic findings", "diagnosis 1", and "diagnosis 2".

In the template display showing a view of partial network information as shown in FIG. 13, the number of options listed is limited to some extent, so that the options become easily readable and can be easily selected. The listed input element items include all of items necessary for inputting data indicative of findings of a radiological report. Even if the network information in the template display is narrowed, entry of data indicative of findings becomes easier, and no problem occurs.

A method of extracting the partial network information from the whole network information will be described.

FIG. 14 is a diagram illustrating a template TP1 for determining extraction conditions (extraction condition determination template) for extracting desired partial network information from the whole network information.

As described above, when a patient is specified by the patient specifying operation, on the radiological report input screen G1 (FIG. 9), for example, the request information (FIG. 11) is displayed in the request display area A1, and the attribute information (FIG. 12) related to patients and examinations is displayed in the examination information display area A3. By the function of the support information retrieving unit 120, the extraction condition determination template TP1 is displayed in the report creating area A4.

As shown in FIG. 14, in the extraction condition determination template TP1, by selecting one word or phrase (option) with respect to each of the attribute items "region classification", "modality", "sex", and "category" as part of all of the attribute items in the whole network information, a combination of options can be designated as an extraction condition. The extraction condition is given to the support information retrieving unit 120 in response to an input from the input client 40.

Concretely, in the extraction condition determination template TP1 shown in FIG. 14, one attribute value (option) can be selected from each of lists PL1 to PL4 by a mouse pointer MP which operates in response to operation of the mouse of the input client 40. By selecting one option with respect to each of the attribute items, adjusting the mouse pointer MP onto the condition determination button DB, and left-clicking the mouse, an extraction condition for designating a combination of options (words or phrases) of the four attribute items can be determined.

The support information retrieving unit 120 retrieves through the input support DB 110 in response to designation of an extraction condition from the input client 40. From the whole network information, partial network information corresponding to the extraction condition is extracted as information for displaying a view as a template in the report creating area A4 (hereinbelow, also called "network information for display"). The support information retrieving unit 120 can extract partial network information satisfying the extraction condition from the whole network information with reference to the count information in the input support DB 110. At this time, partial count information corresponding to the extracted partial network information is also extracted from the count information. The partial network information and the partial count information will be also properly generically called "partial association information".

The region classification, modality, sex, and category in FIG. 14 can be also automatically selected from the request information (FIG. 11) and the attribute information of the patients and examinations (FIG. 12) by selecting a patient list.

FIG. 15 is a flowchart showing the operation flow of narrowing information to be displayed. The operation flow is realized by executing the program for realizing the input support function in the server 100.

In step ST11, the extraction condition determination template TP1 as shown in FIG. 14 is displayed in the report creating area A4.

In step ST12, in response to designation of an option on the extraction condition determination template TP1, data indicative of an extraction condition is entered. For example, a reading physician specifies the region classification "skull", the modality "MRI", and the sex "male (M)" with reference to the request information (FIG. 11) displayed in the radiological report input screen G1 and, by seeing the image display screens M1 and C1, can specify the category "brain infarction". With respect to the four items "region classification", "modality", "sex", and "category", data indicative of a combination of the region classification "skull", the modality "MRI", the sex "M", and the category "brain infarction" can be entered as an extraction condition.

In step ST13, the partial network information satisfying the extraction condition entered in step ST12 is extracted from the input support DB 110 by the support information retrieving unit 120.

In step ST14, a template is provided in which the partial network information extracted in step ST13 is visibly displayed in the report creating area A4. Since the template provided is for supporting an input of findings of a new radiological report, the template can be also called "input support template".

FIG. 16 is a diagram showing a display example of an input support template TP2. Various inputs and designations in the input support template TP2 which will be described later are performed on the basis of a signal output from a report input unit 41 in response to an operation in the input client 40 of the reading physician.

As shown in FIG. 16, in the input support template TP2, a plurality of words or phrases F1, F2, F3, F4, F5, and F6 in the items "category", "image capture condition", "region", "basic findings", "diagnosis 1", and "diagnosis 2", respectively, are displayed in an area of about ¾ from top. Concretely, in the attribute item "category", a plurality of words or phrases ("brain infarction", "ischemic change", . . . ) F1 are listed. In the attribute item "image capture condition", a plurality of words or phrases ("T1 image", . . . and "T2, flair image") F2 are listed. In the attribute item "region", a plurality of words or phrases ("frontal lobe>", . . . and "pons") F3 are listed. In the attribute item "basic findings", a plurality of words or phrases ("point-like and/or tacketic high signal areas", . . . , and "dispersed high signal areas") F4 are listed. In the attribute item "diagnosis 1", a plurality of words or phrases ("old brain infarction", . . . , and "multiple brain infarction") F5 are listed. In the attribute item "diagnosis 2", a plurality of words or phrases (thrombotic infarct", . . . , and "embolic infarct of middle cerebral artery") F6 are listed.

In the item "category", a colored square cursor KS1 is placed on the word or phrase ("brain infarction" in FIG. 16)

designated under the extraction condition. That is, in the input support template TP2, the conditions (words or phrases) already narrowed with respect to the item "category" are shown for confirmation.

In the item "image capture condition", by adjusting a mouse pointer MP onto an image capture condition that matches examination information (FIG. 12) shown in the left examination information display area A3 in the left part and left-clicking the mouse, a colored square cursor KS2 is placed on a desired word or phrase (in FIG. 16, "T2, flair image"). A word or phrase may be designated for the item "image capture condition" by automatically designating an image capture condition that matches examination information by the support information retrieving unit 120.

With respect to the four items "region", "basic findings", "diagnosis 1", and "diagnosis 2", words or phrases associated with each other between the items are connected to each other via lines (in this case, broken lines) on the basis of the partial network information which is extracted under the extraction condition. In such a manner, the partial network information narrowed to some extent is visibly displayed in a view. Therefore, the user can refer to a view in which past knowledge is understood at a glance.

By adjusting the mouse pointer MP on one of the plurality of words or phrases in each of the four items "region", "basic findings", "diagnosis 1", and "diagnosis 2" and left-clicking the mouse, the user can designate a word or a phrase in each of the items constructing findings for a new radiological report.

A word or a phrase with ">" such as the phrase "frontal lobe>" indicates that the word or phrase has smaller elements (region phrase). When the mouse pointer MP is adjusted on a word or a phrase with ">" and right-clicking is performed, a list of commands appears. When "setting of smaller elements" is designated in the list of commands, smaller elements "right frontal lobe", "left frontal lobe", "white material of right frontal lobe", "white material of left frontal lobe", and the like are listed. A desired smaller element can be designated with the mouse pointer MP.

At the time of designating a word or phrase corresponding to each item, a sentence model MD of findings in a radiological report, which is displayed in a lower part of the input support template TP2 is referred to. The sentence model MD is displayed on the basis of data of a report model (sentence model) supplied from the outside together with teaching data and the like.

The sentence model MD is a model of findings of a radiological report such as "in blank W3, blank W4 is/is not found. Blank W5 is suspected. Blank W6 is suspected." In the blanks W3 to W6, words or phrases with respect to element items "region", "basic findings", "diagnosis 1", and "diagnosis 2" are filled, respectively. To be specific, one word or phrase (for example, "frontal lobe") out of a plurality of words or phrases (options F3) is filled in the blank W3. One word or phrase (for example, "high signal area") out of a plurality of words or phrases (options F4) is filled in the blank W4. One word or phrase (for example, "acute stroke") out of a plurality of words or phrases (options F5) is filled in the blank W5. One word or phrase (for example, "acute brain infarction") out of a plurality of words or phrases (options F6) is filled in the blank W6.

At the time of designating words for the four items, first, when the mouse pointer MP is placed on a word or a phrase (designated word or phrase) belonging to one of the four items. By the support information retrieving unit 120, partial count information corresponding to partial network information is referred to. When the number of combinations of options including the designated word or phrase is equal to or larger than a predetermined number of times (for example, 10 times), a line indicative of the combination of options becomes a thick line so as to be emphasized.

For example, as shown in FIG. 16, when one phrase "lacunar infarct" belonging to the item "diagnosis 1" is designated, the display mode of the lines indicative of the combination between the one phrase "lacunar infarct" and plurality of words or phrases belonging to the three items "region", "basic findings", and "diagnosis 2" other than the item "diagnosis 1" to which "lacunar infarct" belongs is changed to, for example, a thick line in accordance with the strength of the relation with "lacunar infarct". By the change in the display mode, a combination of words or phrases which are frequently used in the existing radiological reports can be grasped at a glance. Consequently, by selecting words or phrases in accordance with the combination of words which are frequently used, a radiological report can be created accurately and smoothly. The order of designating words or phrases in the four items is not limited. The user can place the mouse pointer MP on a word or phrase intuitively and select a proper word or phrase with reference to the use frequency or the like. Thus, creation of a radiological report is facilitated.

In the sentence model MD, two options VS are displayed as conclusive words or phrases in a natural sentence along a predetermined sentence model other than the four items. By selecting a radio button provided on the left side of one of the two options VS with the mouse pointer MP, one option (in FIG. 16, "is found") can be designated. The number of options for conclusive words or phrases may be three or more. The other words constructing a natural sentence such as adjective and adverb may be also selectively designated.

The words or phrases designated for the four items and conclusive words or phrases designated by the report input unit 41 as described above are displayed in an area (designated word/phrase list area) SS at the bottom of the input support template TP2. In this case, in response to an input from the report input unit 41, the words or phrases displayed in the designated word/phrase list area SS are input as elements constructing findings of a radiological report along the sentence model MD as a predetermined rule to a report constructing unit 131. The report constructing unit 131 generates data indicative of findings of a new radiological report in accordance with a predetermined rule on the basis of the words or phrases displayed in the designated word/phrase list area SS.

The data indicative of findings of the new radiological report created by the report constructing unit 131 is supplied to the input client 40 and displayed in the findings display area A5. At this time, when a command "findings registration" in the command input area A8 is designated in response to an operation of the input client 40, the data indicative of new radiological report generated by the report constructing unit 131 is added and registered in the diagnosis information DB 210 by the data writing unit 132. By the network information updating operation, the network information is updated. In association with the updating of the network information, the number of lines associating words or phrases increases and the display mode of the lines changes also in the view of the partial network information extracted in accordance with the extraction condition.

As described above, in the information processing system 1 according to the embodiment of the invention, information of the association between elements (words or phrases) belonging to items included in a plurality of elements of a predetermined report is stored in the input support DB 110. Partial information corresponding to an extraction condition designated by the user is extracted from the input support DB 110 and is shown in a view. With such a configuration, the user can create a report while utilizing past knowledge with reference to the view. Thus, the invention can support creation of a report accurately and smoothly.

By adding information of association of elements (words or phrases) in the items to the information accumulated in the input support DB 110 on the basis of information of a new radiological report which is entered by the user, the information stored in the input support DB 110 is updated. Consequently, creation of a report can be supported by effectively utilizing past knowledge which changes with time.

Each time information of a new radiological report corresponding to the association of the elements (words or phrases) is input by the user, information of association of the elements between the items is added to the information in the input support DB 110, thereby updating the input support DB 110. Therefore, the user can always create a report with reference to the latest information.

Since information of association among elements (words or phrases) stored in the input support DB 110 is described in the RDF language, network information can be described easily.

When the user designates elements (words or phrases) to the items in a state where a view of network information displayed visibly in the report creating area A4 is output, the designated elements are input as elements constructing a report along a predetermined report model of findings of a radiological report. With such a configuration, the user can easily enter elements constructing a radiological report.

In the state where a view of network information visibly displayed in the report creating area A4, a plurality of options are displayed for elements (for example, conclusive words or phrases) constructing findings (natural sentence) of a radiological report other than a plurality of attribute items, so that the user can properly designate an option. As a result, on the basis of the designated elements (words or phrases) in the items and the designated option, data indicative of a radiological report along a predetermined report model is created. With such a configuration, the report creating operation can be simplified.

By performing language processing on each of a plurality of pieces of report data stored in the diagnosis information DB 210, information in which elements (words) belonging to items are associated with each other is created. Consequently, by effectively utilizing report data stored in the past, accurate and smooth report creation can be supported.

Since the plurality of pieces of report data stored in the diagnosis information DB 210 include data indicative of a plurality of reports of medical information, report creation in the medical field can be supported.

In the report creating area A4, a view of network information narrowed by the attribute information (information such as the attribute items "region classification", "modality", and "sex") of a radiological report is displayed. Consequently, necessary information can be properly extracted from the information of radiological reports stored in the past, and displayed in a view.

In a view presented in the report creating area A4, a plurality of elements (words or phrases) belonging to a diagnosis are displayed. By employing such a configuration, a radiological report can be created with reference to a plurality of elements used as elements indicative of a diagnosis in past radiological reports. Thus, a report can be created more accurately and smoothly.

In a view presented in the report creating area A4, a plurality of elements showing a category of a diagnosis, a plurality of elements of a region, and a plurality of elements of basic findings are displayed in spatially sequence order. With such a configuration, the user can create data indicative of a radiological report while referring to the plurality of elements belonging to each of the items displayed in the writing order in a radiological report. Thus, report data indicative of a report can be created more accurately and smoothly.

Since a group of candidates of image capture conditions is displayed in a view presented in the report creating area A4, data indicative of the image capture conditions can be easily entered.

Modifications

Although the embodiment of the invention has been described above, the invention is not limited to the above description.

For example, in the foregoing embodiment, whole network information is generated and stored in the input support DB 110, and partial network information according to an input of an extraction condition is extracted and displayed in a view. The invention, however, is not limited to the embodiment but may be applied to other modes described below.

For example, association information is prepared by generating and storing, in the input support DB 110, single report structured data as shown in FIG. 4 with respect to each of all of existing radiological reports stored in the diagnosis information DB 210. In accordance with an input of an extraction condition, the support information retrieving unit 120 collects signal report structured data matching the extraction condition. When it is assumed that a combination of the region classification "skull", the modality "MRI", the sex "M", and the category "brain infarction" is entered as an extraction condition with respect to the four items "region classification", "modality", "sex", and "category", all of single report structured data having the combination of attribute information is detected from the input support DB 110. On the basis of the detected multitudes of pieces of single report structured data, as shown in FIG. 13, attribute values (words or the like) are listed in attribute items other than the item used for the extraction condition, and network information in which a plurality of attribute values in the attribute items are associated with each other between the attribute items so as to form a network is created. At the time of creating the network information, the number of times of the combination of the associated words or phrases between the items in the single report structured data is counted, and the count information is stored in the input support DB 110. The created network information is visually output (displayed) in the report creation area A4, and a template for supporting an entry of report data indicative of a radiological report is provided.

Also with such a configuration, effects similar to those of the foregoing embodiment can be obtained.

When a number of pieces of single report structured data stored in the input support DB 110 are seen as a whole, it can be also regarded as network information in which a plurality of attribute values belonging to the respective attribute items are associated with each other between the attribute items so as to form a network. In this case, it can be also regarded that partial network information as part of the whole network information is extracted in response to an extraction condition and visibly output (displayed) in a view.

With such a configuration, a search using a number of pieces of single report structured data stored in the input support DB 110 can be conducted. For example, when a keyword is simply entered from the input client 40, report data indicative of a radiological report including a word or phrase matching the keyword is detected by the support information retrieving unit 120 on the basis of the multitudes of pieces of single report structured data stored in the input support DB 110, and the detected report data indicative of the radiological report may be extracted from the diagnosis information DB 210 and visually output (displayed) in the input client 40. It is also possible to detect a radiological report satisfying two conditions that a phrase in the item "region" is "frontal lobe" and a phrase in the item "diagnosis 1" is "lacunar infarct" on the basis of the multitudes of single report structured data stored in the input support DB 110, and visually output (display) the detected report data indicative of the radiological report in the input client 40.

As described above, because of the function of detecting report data corresponding to a retrieval condition entered by the user from a database that stores a plurality of pieces of report data, the user can properly obtain required information.

Although a view is displayed in the report creating area A4 on the basis of partial network information of the whole network information stored in the input support DB 110 in the embodiment, the invention is not limited to the embodiment. For example, when the number of items in the whole network information and the number of elements belonging to each of the items are small to some extent, a view may be displayed in the report creating area A4 on the basis of the whole network information stored in the input support DB 110.

Figure 17:
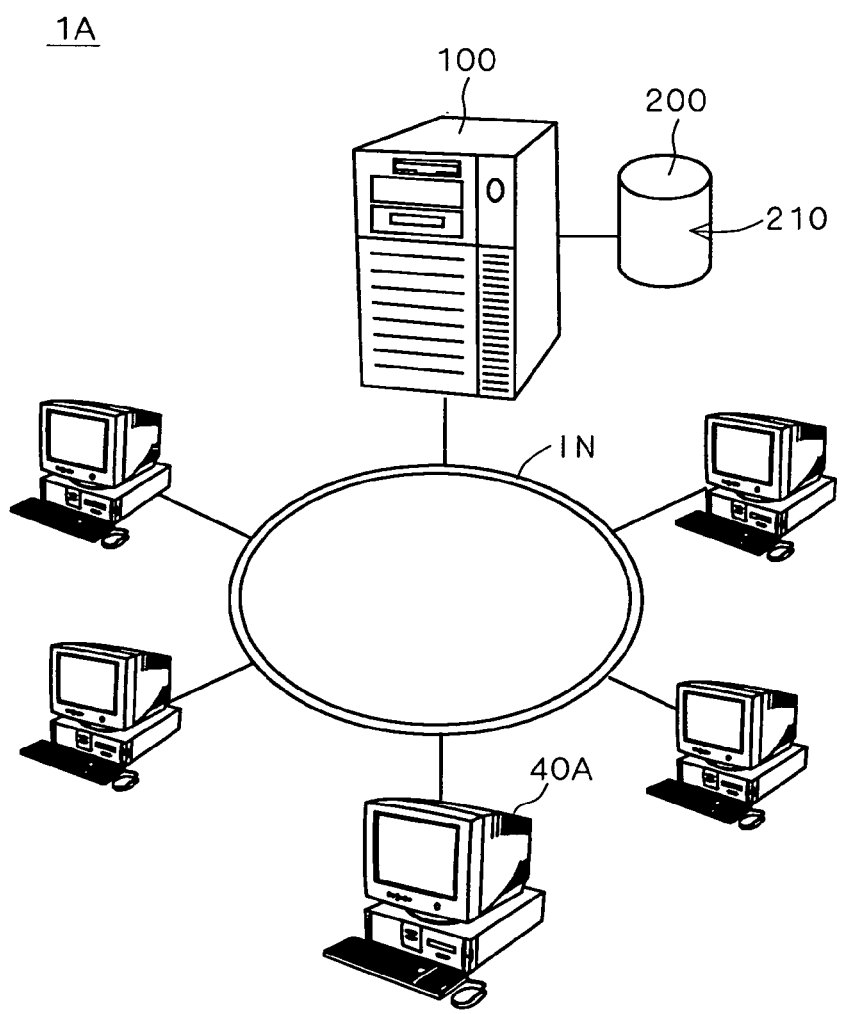
FIG. 17 is a diagram showing an outline of an information processing system as a modification.

Although the input support function using, as past knowledge, report data indicative of radiological reports accumulated in a hospital in which the server 100 and the terminals 10 to 60 are connected to each other via the network NTW or the like in the hospital so that data can be transmitted/received has been provided in the foregoing embodiment, the invention is not limited to the embodiment. Alternatively, a configuration as shown in FIG. 17 may be also employed. In the configuration, a company for providing services of supporting entry of report data indicative of a radiological report or a specified hospital has the server 100. A reading physician in any of other hospitals accesses the server 100 via an internet line IN or the like by using a terminal (for example, a terminal 40A for entering reports), and uses the input support function. In this case, a company or the like having the server 100 may provide services for holding data indicative of images, report data indicative of radiological reports, and the like of the hospitals.

In the foregoing embodiment, partial network information is extracted from the whole network information on the basis of an extraction condition that designates a combination of elements of items as part of a plurality of attribute items of the whole network information. However, the invention is not limited to the embodiment. Alternatively, it is also possible to extract partial network information from the whole network information on the basis of an extraction condition of designating elements of one item (for example, category) included in a plurality of attribute items of the whole network information. With such a configuration, the amount of information displayed in a view can be limited, so that visibility of a template can be improved.

In the foregoing embodiment, each time report data indicative of a new radiological report is entered, past knowledge is changed. Consequently, each time the data writing unit 132 receives an entry of report data indicative of a new radiological report as new input information from the report constructing unit 131, the association among elements belonging to the different items is changed, thereby improving display in a view. In such a mode, the user can always create a piece of report data with reference to the latest information. However, there may be users who feel uncomfortable when display in a view in the report creating area A4 changes frequently. Consequently, the association among elements belonging to the items may be changed on the basis of newly entered input information at predetermined timings such as once a week or once a month. That is, a batch process of storing new input information for a certain period of time and making the information reflected in a lump into the past knowledge may be performed. With such a configuration, low operability which may occur due to frequent changes in display in a view can be avoided.

In the foregoing embodiment, an example of supporting an entry of report data indicative of a radiological report has been described and report data of a number of radiological reports is used as past knowledge. The invention is not limited to the embodiment. For example, to support an entry of report data indicative of a report of other medical information such as an incident report and a diagnosis report, reports of other medical information such as a number of incident reports, diagnosis reports, and nursing diaries may be used as past knowledge.

Further, the invention is not limited to the case of supporting an entry of report data indicative of a report of medical information in a medical institute but can be also generally applied to the case of supporting, for example, an entry of report data indicative of various reports such as a sales report.

Although information accumulated in the input support DB 110 is created by analyzing existing report data indicative of radiological reports in the foregoing embodiment, the invention is not limited to the embodiment. For example, by supplying words or phrases to items from medical knowledge, part or all of information accumulated in the input support DB 110 is generated. In such a manner, knowledge may be accumulated. Alternatively, a function of properly adding an item may be added.

Although the process in the identifying unit 105 is performed so as to replace all of variations in expression and synonyms with the most frequently used one in the foregoing embodiment, for example, the process in the identifying unit 105 may be performed as follows. While replacing all of variations in expression and synonyms with the most frequently used one, elements (such as expressions and words or phrases) in the report creating area A4 and report data indicative of radiological reports may be customized in accordance with the users and displayed.

Although words or phrases corresponding to items constructing findings of a new radiological report are designated by placing the mouse pointer MP on one of a plurality of words or phrases and left-clicking the mouse in each of the four items "region", "basic findings", "diagnosis 1", and "diagnosis 2", the invention is not limited to the embodiment.

For example, as shown in FIG. 15, at the time of designating the phrase "lacunar infarct" in the item "diagnosis 1" as part of the four items as an element of report data indicative of a new radiological report, in the case where words or phrases in the items "region", "basic findings", and "diagnosis 2" other than the item "diagnosis 1" as part of the four items are unconditionally associated with the phrase "lacunar infarct" which is already designated to "diagnosis 1" as part of the items in the network information visibly output to the input support template TP2, the words or phrases (for example, in FIG. 15, the phrase "point-like high signal area" and the phrase "embolic infarct of anterior cerebral artery" associated with the phrase "lacunar infarct" via the thick line) unconditionally associated with the other items "region", "basic findings", and "diagnosis 2" may be automatically designated as elements constructing report data indicative of a new radiological report.

Although a concrete example of operation of automatically designating words or phrases unconditionally associated with an already designated word or phrase has been described above, similar operation may be applied to other items and other words or phrases. Although a word or phrase in a frequently-used combination, which is unconditionally associated with thick lines is automatically designated in the above concrete example, a word or phrase in a not-frequently-used combination, which is unconditionally associated with broken lines may be automatically designated.

As described above, by employing the configuration of automatically designating elements belonging to the other items unconditionally associated with an element (word or phrase) designated in response to an operation of the user for an item as part of the items, the report creating operation can be further simplified.

Although a plurality of words or phrases as a plurality of elements belonging to the different items are stored so as to be associated with each other in the input support DB 110 in the foregoing embodiment, the invention is not limited to the embodiment. For example, in the case where elements other than words or phrases such as figures and images are included in a report, elements other than words or phrases such as a plurality of figures or images may be included in a plurality of elements belonging to each of the items.

Concretely, for example, when figures or images of characteristic cases are associated with words or phrases belonging to the item "diagnosis 1" and the phrase "lacunar infarct" is designated for the item "diagnosis 1" on the radiological report input screen G1, the figure or image (for example, FIG. 18) of the characteristic case associated with the "lacunar infarct" may be displayed or inserted in the image attaching area A7 or the like. Such a figure or image of the characteristic case may be displayed as a popup image when the mouse pointer MP is placed on the words "lacunar infarct".

Figure 19A:
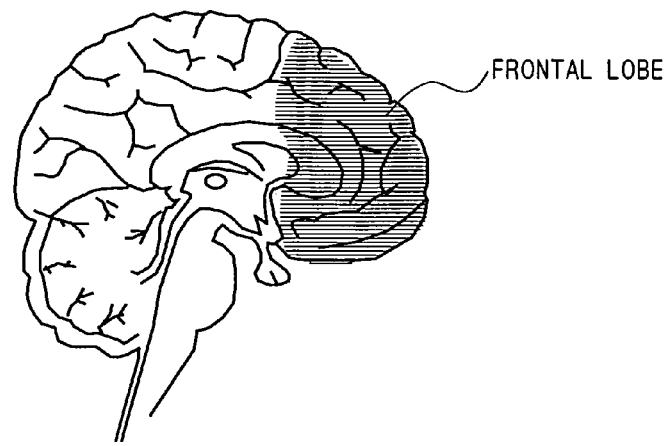
FIGS. 19A, 19B, and 19C are diagrams illustrating display elements of a modification.
Figure 19B:
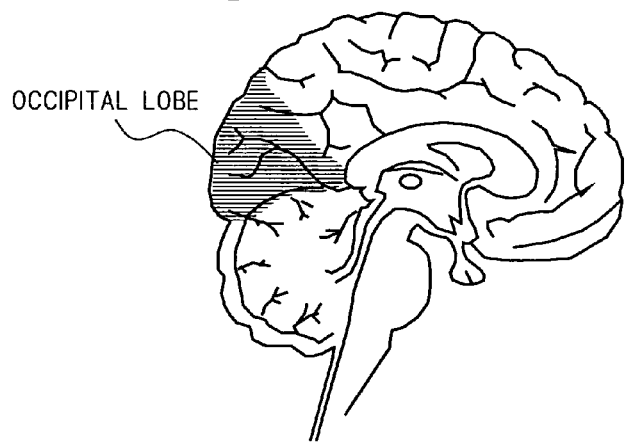
Figure 19C:
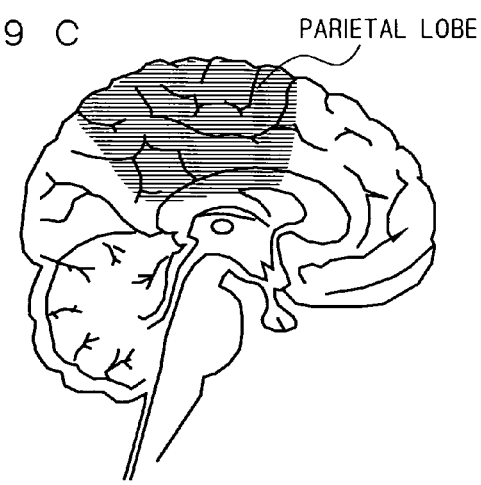
Figure 20A:
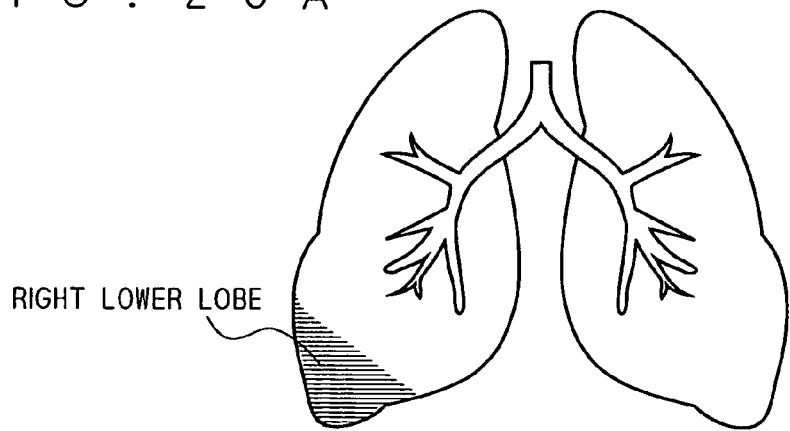
FIGS. 20A, 20B, and 20C are diagrams illustrating display elements of a modification.
Figure 20B:
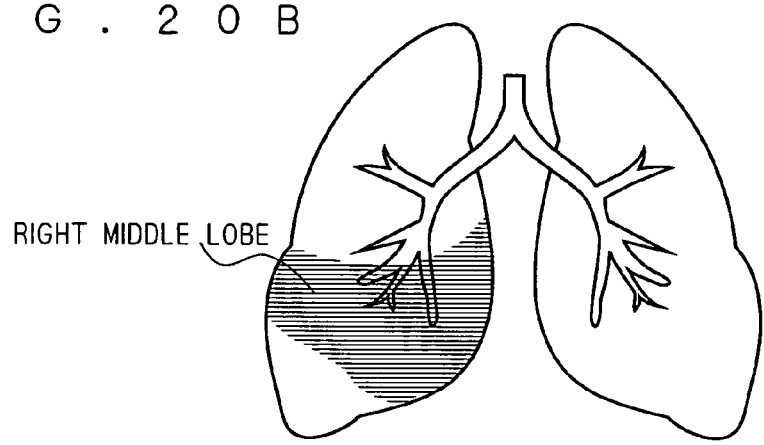
Figure 20C:
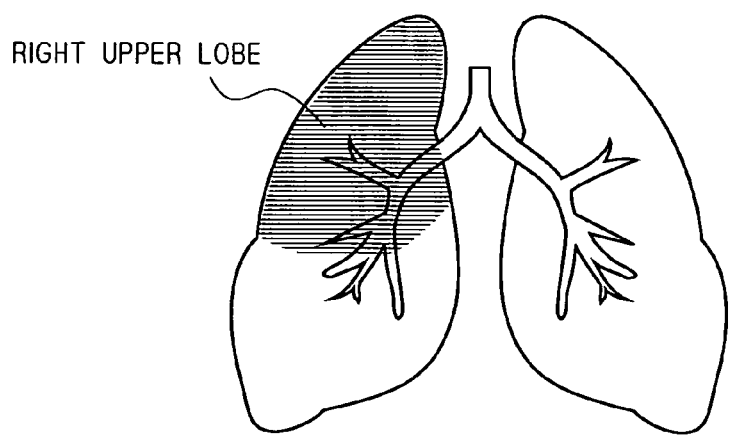

In place of a plurality of words or phrases belonging to the item "region", a plurality of figures indicative of regions corresponding to a plurality of words or phrases may be employed. For example, three regions "frontal lobe", "occipital lobe", and "parietal lobe" of the brain may be expressed by figures as shown in FIGS. 19A, 19B, and 19C, respectively. When figures as shown in FIGS. 19A to 19C are used in place of a plurality of words or phrases in the report creating area A4, at the time of creating report data indicative of a radiological report while watching CT or MR images of a patient, the user can easily select a region intuitively. The figures, images, or the like of regions are not limited to those shown in FIGS. 19A to 19C. Figures, images, or the like showing various regions such as figures showing parts of a lung as shown in FIGS. 20A to 20C can be employed.

Figure 21A:
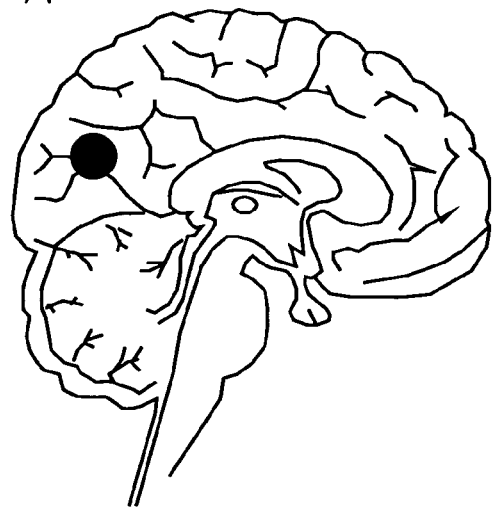
FIGS. 21A, 21B, and 21C are diagrams illustrating display elements of a modification.
Figure 21B:
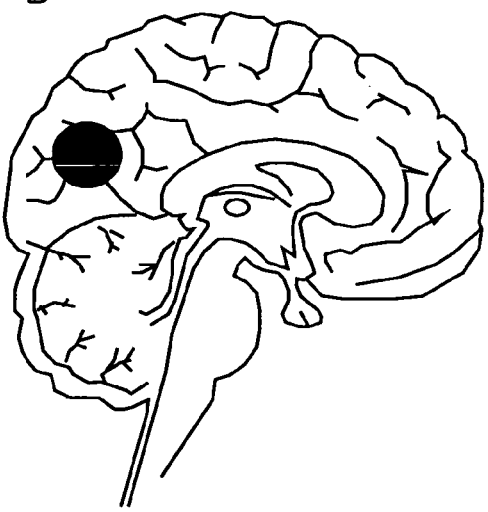
Figure 21C:
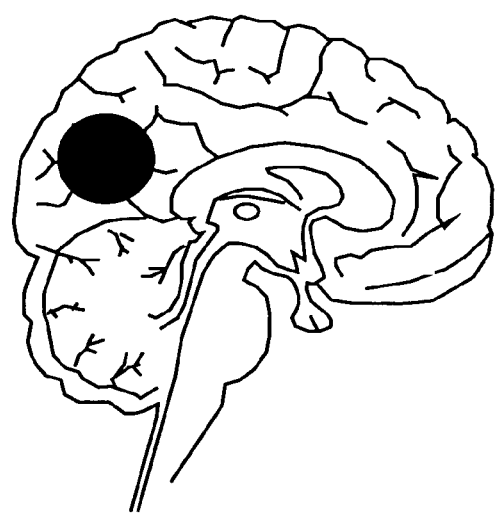

When the user wishes to enter, for example, the size of an infarct, tumor, or the like in the item "diagnosis 1", in this case, figures showing the size (specified by a painted circle in the diagrams) as shown in FIGS. 21A, 21B, and 21C may be employed. For example, in place of words or phrases such as "a tumor of three centimeters in length and width", a figure as shown in FIG. 21A may be employed.

As described above, at the time of associating a plurality of elements belonging to the items including figures or the like with each other between the items in the input support DB 110, when the whole network information stored in the input support DB 110 is written in the RDF language, by describing the figure by using the URL while separately storing the information of the diagram itself, the words or phrases and the information of the figure can be associated with each other. To include information of a figure or the like in the information stored in the input support DB 110, at the time of analyzing report data indicative of existing reports and structuring elements constructing the reports so as to be associated with each other, the information of the figure or the like has to be extracted and associated.

In the method, first, teaching data obtained by adding information of various figures to a corpus for learning is prepared and the machine learning is performed. Also at the time of analyzing the report data indicative of the existing reports by using machine-learnt information, words or phrases are extracted with respect to each of the items, the information of the figures is extracted by using a method such as pattern matching, and single report structured data including the figures can be generated.

Alternatively, all of information (attribute information) of report data indicative of existing reports used at the time of creating the whole network information, such as data indicative of original findings, an original radiological report, or the like may be associated as elements with the whole network information stored in the input support DB 110. In the case of associating the information with the data indicative of original findings, by narrowing elements belonging to the items by a retrieving function using the whole network information or the like, the original findings can be extracted easily. As a result, the original findings or the like can be easily corrected or changed.

Although information of the item "sex" is included in the network information shown in FIG. 5 in the foregoing embodiment, obviously, other information included in single report structured data, for example, information of the item "age" may be included in network information. For example, a condition related to the item "age" may be added to extraction conditions of extracting partial network information from the whole network information. As described above, in the case where the age is added as a condition and tendencies of symptoms vary according to ages such as young age and middle age, creation of report data indicative of a radiological report can be further facilitated such as the case of creating report data indicative of a radiological report.

In the foregoing embodiment, by designating elements belonging to the items displayed in the report creating area A4, report data indicative of a new radiological report can be created. As a result, new information corresponding to the association among elements belonging to the items can be entered. However, the invention is not limited to the embodiment. For example, the user may directly enter data indicative of elements such as words or phrases to a plurality of items without designating displayed elements belonging to the items with respect to part or all of the plurality of items displayed in the report creating area A4.

Concretely, words or phrases belonging to items may be designated by directly entering words or phrases to blanks W3 to W6 with a keyboard by the user without designating words or phrases from the plurality of words or phrases F3 to F6 displayed in the report creating area A4. With such a configuration, while designating words or phrases belonging to the items from the plurality of words F3, F5, and F6 on the items "region", "diagnosis 1", and "diagnosis 2" on the screen shown in FIG. 16, a word or phrase is directly entered to the blank W4 with respect to the item "basic findings", thereby enabling information corresponding to the association of elements belonging to the items between the items to be entered. Since past knowledge is changed also by new input information corresponding to the association in the elements belonging to the items between the items, the support DB 110 is properly updated.

While the invention has been shown and described in detail, the foregoing description is in all aspects illustrative and not restrictive. It is therefore understood that numerous modifications and variations can be devised without departing from the scope of the invention.

What is claimed is:

1. An information processing system comprising:
  a first storage for storing an association information database in which association information is stored, said association information being information indicative of association between a plurality of words or phrases belonging to respective classifications in a one-to-one corresponding manner and wherein said plurality of words or phrases are associated with said classifications and furthermore, said plurality of words or phrases are associated in a direction between said classifications;
  an information extracting unit, in response to designation of an extraction condition of a user, for extracting partial association information corresponding to said extraction condition from said association information database;
  a display for visibly outputting a view of network information in accordance with said partial association information, said network information being information in which said plurality of words or phrases elements belonging to said classifications are associated with said classifications to form a network that includes said network information, wherein said view of network information visibly output on said display comprises 1) a plurality of said classifications, 2) a plurality of sets of words or phrases that correspond in a one-to-one manner to said plurality of said classifications, 3) a visual marker that illustrates that said plurality of words or phrases are associated in said direction between said classifications;
  a designating unit for designating a word or phrase in response to an input of a user in said view of said network information; and
  an element input unit for inputting a first set of plurality of words or phrases designated by said designating unit as a second set of plurality of words or phrases constructing a piece of report data according to a predetermined report model.

2. The information processing system according to claim 1, wherein said extraction condition includes a condition of designating a single word or phrase belonging to one of said classifications or a combination of words or phrases belonging to said classifications in a one-to-one corresponding manner as a part of said classifications.

3. The information processing system according to claim 1, wherein said association information includes information in which said plurality of words or phrases belonging to said classifications are associated with each other between said classifications so as to form said network.

4. The information processing system according to claim 1, further comprising:
  an information accepting unit for accepting input information in response to an input operation of a user, said input information being information corresponding to a combination of words or phrases belonging to said classifications in a one-to-one corresponding manner; and
  an information updating unit for updating said association information database by adding information indicative of association of words or phrases belonging to said classifications in a one-to-one corresponding manner to said association information in accordance with said input information.

5. The information processing system according to claim 1, wherein said association information includes information written in RDF language.

6. The information processing system according to claim 1, wherein said display displays a plurality of word or phrase options for one word or phrase in a piece of report data according to said predetermined report model other than said plurality of sets of words or phrases with said view of said network information,
  said designating unit designates one of said word or phrase options from said plurality of word or phrase options in response to an input of a user on said display,
  said element input unit inputs said one of said word or phrase options as one word or phrase of said piece of report data according to said report model, and
  said information processing system further comprises a report generating unit for generating said piece of report data according to said report model in accordance with said plurality of words or phrases entered by said element input unit.

7. The information processing system according to claim 1, wherein when words or phrases are designated to said classifications in response to an input of a user in said view of said network information, in a case where a combination of said plurality of words or phrases designated to said classifications as said part of said plurality of classifications has been already unconditionally associated with one predetermined word or phrase belonging to a classification other than said plurality of classifications as said part of said classifications in said network information, said designating unit designates said one predetermined word or phrase to said classification other than said classifications as said part of said classifications.

8. The information processing system according to claim 1, further comprising:
  a second storage for storing a report database in which a plurality of pieces of report data are stored; and
  an information generating unit for generating said association information by performing a predetermined information processing including a language processing on said plurality of pieces of report data.

9. The information processing system according to claim 1, wherein each of said plurality of words or phrases is alphanumeric data.

10. The information processing system according to claim 1, further comprising:
  a display mode changing unit, in response to designation of one word or phrase by a user in said view of said network information, for changing a display mode showing at least one association between said one word or phrase and other words or phrases different from said one word or phrase to a mode according to at least one degree of association, wherein:
  said display mode visually identifies on said display a strength of a relation between said one word or phrase and each of said other words or phrases different from said one word or phrase; and
  wherein said plurality of words or phrases input by said element input unit are utilized by said element input unit for updating a degree of association among said plurality of words or phrases input by said element unit in said association information database.

11. The information processing system according to claim 1, wherein said association information comprises a count of a number of combinations of said plurality of words or phrases.

12. The information processing system according to claim 1, further comprising:
   a data reading unit that reads textual information;
   a natural sentence structuring unit that receives said textual information read by said data reading unit and disassembles said textual information into said plurality of words or phrases; and
   a means for generating said association information database from said plurality of words or phrases and for sending said association information database to said first storage.

13. The information processing system according to claim 1, wherein a thickness of said visual marker is determined as a function of strength of association between said words or phrases and said classifications.

14. The information processing system according to claim 1, wherein said visual marker is a non-textual representation of strength of association between said words or phrases and said classifications.

15. The information processing system according to claim 4, wherein said information updating unit updates said association information database by adding information indicative of association of said words or phrases belonging to said classifications in a one-to-one corresponding manner to said association information each time said information accepting unit accepts said input information.

16. The information processing system according to claim 4, wherein said information updating unit updates said association information database by adding information indicative of association of said words or phrases belonging to said classifications in a one-to-one corresponding manner to said association information at a predetermined timing.

17. The information processing system according to claim 8, further comprising:
   a retrieval condition input unit for inputting a retrieval condition in response to an operation of a user; and
   a data detector for detecting at least one piece of report data corresponding to said retrieval condition from said plurality of pieces of report data stored in said report database.

18. The information processing system according to claim 8, wherein said plurality of pieces of report data include data indicative of a plurality of medical information reports.

19. The information processing system according to claim 9, wherein said alpha-numeric data comprises a word.

20. The information processing system according to claim 9, wherein said alpha-numeric data comprises a phrase of words.

21. The information processing system according to claim 10, wherein each of said plurality of words or phrases is alpha-numeric data.

22. The information processing system according to claim 18, wherein said plurality of medical information reports include a plurality of incident reports.

23. The information processing system according to claim 18, wherein said plurality of medical information reports include a plurality of diagnosis reports.

24. The information processing system according to claim 18, wherein said plurality of medical information reports include a plurality of radiological reports.

25. The information processing system according to claim 21, wherein said alpha-numeric data comprises a word.

26. The information processing system according to claim 21, wherein said alpha-numeric data comprises a phrase of words.

27. The information processing system according to claim 24, wherein said plurality of classifications visibly output on said display include diagnosis.

28. The information processing system according to claim 24, wherein said plurality of classifications include a category of diagnosis, a region, and a basic finding.

29. The information processing system according to claim 24, wherein said classifications include an image capture condition, and
   said display displays a plurality of words or phrases belonging to said image capture condition in said view of said network information.

30. An information processing system comprising:
   a first storage for storing an association information database in which association information is stored, said association information being information indicative of association between words or phrases belonging to respective classifications in a one-to-one corresponding manner and wherein said words or phrases are associated with said classifications and furthermore, said plurality of words or phrases are associated in a direction between said classifications;
   an information accepting unit for accepting input information in response to an input operation of a user, said input information being information corresponding to a combination of words or phrases belonging to said classifications in a one-to-one corresponding manner;
   an information updating unit for updating said association information database by adding information indicative of association of said combination of words or phrases belonging to said classifications to said association information in accordance with said input information;
   a display for visibly outputting a view of network information in accordance with said association information database, said network information being information in which said combination of words or phrases belonging to said classifications are associated with each other between said classifications so as to form a network that includes said network information, wherein said view of network information visibly output on said display comprises 1) a plurality of said classifications, 2) a plurality of sets of words or phrases that correspond in a one-to-one manner to said plurality of said classifications, 3) a visual marker that illustrates that said plurality of words or phrases are associated in said direction between said classifications;
   a designating unit for designating one word or phrase for each classification included in said plurality of said classifications in response to an input of a user in said view of said network information; and
   an element input unit for inputting a plurality of words or phrases designated by said designating unit as a plurality of words or phrases constructing a piece of report data according to a predetermined report model.

31. The information processing system according to claim 30, wherein said information updating unit updates said association information database by adding information indicative of association of words or phrases belonging to said classifications in a one-to-one corresponding manner to said association information each time said information accepting unit accepts said input information.

32. The information processing system according to claim 30, wherein said information updating unit updates said association information database by adding information indicative of association of words or phrases belonging to said classifications in a one-to-one corresponding manner to said association information at a predetermined timing.

33. The information processing system according to claim 30, wherein said association information includes information written in RDF language.

34. The information processing system according to claim 30, wherein said display displays a plurality of word or phrase options for one word or phrase in said piece of report data according to said predetermined report model other than said plurality of words or phrases with said view of said network information,
said designating unit designates one word or phrase element option from said plurality of word or phrase options in response to an input of a user on said display,
said element input unit inputs said one word or phrase option as one word or phrase of said piece of report data according to said report model, and
said information processing system further comprises a report generating unit for generating said piece of report data according to said report model in accordance with a plurality of words or phrases entered by said element input unit.

35. The information processing system according to claim 30, wherein when words or phrases are designated to a classification as a part of said plurality of said classifications in response to an input of a user in said view of said network information, in a case where a combination of a plurality of words or phrases designated to said plurality of said classifications has been already unconditionally associated with one predetermined word or phrase belonging to a classification other than said plurality of said classifications, said designating unit designates said one predetermined word or phrase to said classification other than said plurality of said classifications.

36. The information processing system according to claim 30, further comprising:
a second storage for storing a report database in which a plurality of pieces of report data are stored; and
an information generating unit for generating said association information by performing a predetermined information processing including a language processing on said plurality of pieces of report data.

37. The information processing system according to claim 30, wherein each of said plurality of words or phrases is alpha-numeric data.

38. The information processing system according to claim 30, further comprising:
a display mode changing unit, in response to designation of one word or phrase by a user in said view of said network information, for changing a display mode showing at least one association between said one word or phrase and other words or phrases different from said one word or phrase to a mode according to at least one degree of association, wherein:
said display mode identifies a strength of a relation between the said one word or phrase and each of said other words or phrases different from said one word or phrase; and
wherein said plurality of words or phrases input by said element input unit are utilized by said element input unit for updating a degree of association among said plurality of words or phrases input by said element input unit in an association information database.

39. The information processing system according to claim 30, wherein said association information comprises a count of a number of combinations of said plurality of words or phrases.

40. The information processing system according to claim 30, further comprising:
a data reading unit that reads textual information;
a natural sentence structuring unit that receives said textual information read by said data reading unit and disassembles said textual information into said plurality of words or phrases; and
a means for generating said association information database from said plurality of words or phrases and for sending said association information database to said first storage.

41. The information processing system according to claim 30, wherein a thickness of said visual marker is determined as a function of strength of association between said words or phrases and said classifications.

42. The information processing system according to claim 30, wherein said visual marker is a non-textual representation of strength of association between said words or phrases and said classifications.

43. The information processing system according to claim 36, further comprising:
a retrieval condition input unit for inputting a retrieval condition in response to an operation of a user; and
a data detector for detecting at least one piece of report data corresponding to said retrieval condition from said plurality of pieces of report data stored in said report database.

44. The information processing system according to claim 36, wherein said plurality of pieces of report data include data indicative of a plurality of medical information reports.

45. The information processing system according to claim 37, wherein said alpha-numeric data comprises a word.

46. The information processing system according to claim 37, wherein said alpha-numeric data comprises a phrase of words.

47. The information processing system according to claim 38, wherein each of said plurality of words or phrases is alpha-numeric data.

48. The information processing system according to claim 44, wherein said classifications include diagnosis.

49. The information processing system according to claim 44, wherein said classifications include a category of diagnosis, a region, and a basic finding.

50. The information processing system according to claim 44, wherein said classifications include an image capture condition, and
said display displays a plurality of words or phrases belonging to said image capture condition in said view of said network information.

51. The information processing system according to claim 47, wherein said alpha-numeric data comprises a word.

52. The information processing system according to claim 47, wherein said alpha-numeric data comprises a phrase of words.

* * * * *